(12) United States Patent
Yan et al.

(10) Patent No.: US 9,682,070 B2
(45) Date of Patent: *Jun. 20, 2017

(54) METHOD AND COMPOSITIONS FOR TREATMENT OR PREVENTION OF INFLAMMATORY CONDITIONS

(71) Applicant: University of Rochester, Rochester, NY (US)

(72) Inventors: Chen Yan, Rochester, NY (US); Jian-Dong Li, Marietta, GA (US); Bradford Berk, Rochester, NY (US); Kye-Im Jeon, Rochester, NY (US); Xiangbin Xu, Rochester, NY (US)

(73) Assignee: University of Rochester, Rochester, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/970,028

(22) Filed: Dec. 15, 2015

(65) Prior Publication Data

US 2016/0256444 A1 Sep. 8, 2016

Related U.S. Application Data

(63) Continuation of application No. 14/191,219, filed on Feb. 26, 2014, now Pat. No. 9,241,932, which is a continuation of application No. 12/678,352, filed as application No. PCT/US2008/076475 on Sep. 16, 2008, now abandoned.

(60) Provisional application No. 60/973,998, filed on Sep. 20, 2007.

(51) Int. Cl.
| | |
|---|---|
| A61K 31/4375 | (2006.01) |
| A61K 31/573 | (2006.01) |
| A61K 45/06 | (2006.01) |
| A61K 9/00 | (2006.01) |

(52) U.S. Cl.
CPC ........ *A61K 31/4375* (2013.01); *A61K 9/0046* (2013.01); *A61K 31/573* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 4,033,969 | A | 7/1977 | Sevenet et al. |
| 4,145,552 | A | 3/1979 | Heymes |
| 4,285,949 | A | 8/1981 | Hannart et al. |
| 4,364,947 | A | 12/1982 | Toyomaki |
| 4,749,707 | A | 6/1988 | Calvo et al. |
| 7,041,704 | B2 | 5/2006 | Burgard et al. |
| 9,241,932 | B2 | 1/2016 | Yan et al. |
| 2002/0182196 | A1 | 12/2002 | McCleary |
| 2003/0162824 | A1 | 8/2003 | Krul |
| 2004/0067986 | A1 | 4/2004 | Sassover |
| 2004/0087653 | A1 | 5/2004 | Manning |
| 2004/0156859 | A1 | 8/2004 | Ezrin et al. |
| 2004/0220187 | A1 | 11/2004 | Stephenson et al. |
| 2005/0014722 | A1 | 1/2005 | Jhon et al. |
| 2006/0062739 | A1 | 3/2006 | Hofmann et al. |
| 2006/0183684 | A1 | 8/2006 | Cedarbaum et al. |
| 2007/0116729 | A1 | 5/2007 | Palepu |
| 2007/0117775 | A1 | 5/2007 | Payan |
| 2008/0220084 | A1 | 9/2008 | Fan et al. |

FOREIGN PATENT DOCUMENTS

| | | |
|---|---|---|
| EP | 0305181 A1 | 3/1989 |
| FR | 2469180 A1 | 5/1981 |
| WO | 2005/007672 A2 | 1/2005 |

OTHER PUBLICATIONS

PCT International Search Report and Written Opinion for PCT/US2008/076475 (filed Sep. 16, 2008).
Supplemental European Search Report dated Sep. 1, 2010, for EP 08831827.4.
Balestreri et al. "A Double-blind Placebo Controlled Evaluation of the Safety and Efficacy of Vinpocetine in the Treatment of Patients With Chronic Vascular Senile Cerebral Dysfunction," J. Am. Geriatr. Soc. 35(5):425-430 (1987) (abstract only).
Bereczki et al. "A Systematic Review of Vinpocetine Therapy in Acute Ischaemic Stroke," Eur. J. Clin. Pharmacal. 55:349-352 (1999).
Block, "The Excitement of Vinpocetine," Life Enhancement Products (1999).
Bonoczk et al. "Role of Sodium Channel Inhibition in Neuroprotection: Effect of Vinpocetine," Brain Research Bulletin 53(3):245-254 (2000).
Brown et al. (Toxicology Letters, 168:1-6, 2007, available online Nov. 6, 2006).
Kweon et al. "Synergistic Activation of NF-kB by Nontypeable H. influenzae and S. pneumoniae Is Mediated by CK2, IKKb-IkBa, and p38 MAPK," Biochem.Biophys. Res. Comm. 351:368-375 (2006).
Prokopova et al., "Effect of Vinpocetine on Rat Adjuvant Arthritis," Internal. N. Immunopath. and Pharmacal. 5 (3):193-199 (1992).
Shuto et al. "Activation of NF-kB by Nontypeable Hemophilus influenzae Is Mediated by Toll-like Receptor 2-TAK1-dependent NIK-IKKa/b-IkBa and MKK3/6-p38 MAP Kinase Signaling Pathways in Epithelial Cells," Proc. Nat'l Acad. Sci. USA 98(15):8774-8779 (2001).
Watanabe et al. "Synergistic Activation of NF-kB by Nontypeable Haemophilus influenzae and Tumor Necrosis Factor alpha," Proc. Nat'l Acad. Sci. USA 101(10):3563-3568 (2004).

*Primary Examiner* — Bong-Sook Baek
(74) *Attorney, Agent, or Firm* — Kilpatrick Townsend & Stockton, LLP

(57) ABSTRACT

Pharmaceutical compositions and methods for treating or preventing an inflammatory condition in a patient are disclosed. The pharmaceutical compositions and methods include the use of vincamine or a vincamine derivative, either alone or in combination with one or more additional therapeutic agents, including a steroid (preferably a corticosteroid), an angiotensin II receptor (type 1) antagonist, an angiotensin-converting enzyme (ACE) inhibitor, and a nonsteroidal anti-inflammatory drug.

12 Claims, 17 Drawing Sheets polymorphonuclear neutrophil (PMN)

METHOD AND COMPOSITIONS FOR TREATMENT OR PREVENTION OF INFLAMMATORY CONDITIONS

This application is a continuation of U.S. application Ser. No. 14/191,219, filed Feb. 26, 2014, which is a continuation of U.S. application Ser. No. 12/678,352, filed May 11, 2010 (abandoned), which is a U.S. national phase application of International Application No. PCT/US2008/076475, filed Sep. 16, 2008, which claims the priority benefit of U.S. Provisional patent application Ser. No. 60/973,998, filed Sep. 20, 2007, which is hereby incorporated by reference in its entirety.

STATEMENT AS TO RIGHTS TO INVENTIONS MADE UNDER FEDERALLY SPONSORED RESEARCH AND DEVELOPMENT

This invention was made with government support under HL077789 and DC005843 awarded by the National Institutes of Health. The government has certain rights in the invention.

REFERENCE TO A "SEQUENCE LISTING," A TABLE, OR A COMPUTER PROGRAM LISTING APPENDIX SUBMITTED AS AN ASCII TEXT FILE

The present application contains a Sequence Listing written in file 056777-000330US-0967318_SequenceListing.txt created on May 26, 2016, 6,717 bytes, machine format IBM-PC, MS-Windows operating system. The Sequence Listing is hereby incorporated by reference into the present specification in its entirety.

FIELD OF THE INVENTION

The present invention relates to the use of vincamine derivatives for treating or preventing an inflammatory condition, and pharmaceutical compositions useful for practicing these therapeutic or preventative treatments.

BACKGROUND OF THE INVENTION

Inflammation is a hallmark of a variety of important human diseases, such as atherosclerosis (Libby et al., "Inflammation and Atherosclerosis," *Circulation* 105:1135-43 (2002); Libby, "Inflammation in Atherosclerosis," *Nature* 420:868-74 (2002)), lung inflammatory disease (Tetley, "Inflammatory Cells and Chronic Obstructive Pulmonary Disease," *Curr Drug Targets Inflamm Allergy* 4:607-18 (2005)), and arthritis (Okamoto, "NF-κB and Rheumatic Diseases," *Endocr Metab Immune Disord Drug Targets* 6:359-72 (2006)), etc. Over the past decades, steroids have been used as the main therapeutic anti-inflammatory agent. However, while steroids indeed exhibit a potent anti-inflammatory effect, the extensive usage of steroids also results in significant detrimental effects in patients. Thus, there is an urgent need for development of novel anti-inflammatory agents.

The nuclear-factor κB (NF-κB) is a key transcriptional factor involved in regulating expression of pro-inflammatory mediators including cytokines, chemokines, and adhesion molecules (Kunsch et al., "Oxidative Stress as a Regulator of Gene Expression in the Vasculature," *Circ Res* 85:753-66 (1999)), thereby playing a critical role in mediating inflammatory responses. NF-κB is a dimeric transcription factor consisting of homo- or heterodimers of Rel-related proteins (Ghosh et al., "NF-κB and Rel Proteins: Evolutionarily Conserved Mediators of Immune Responses," *Annu Rev Immunol* 16:225-60 (1998)). In the inactive state, NF-κB resides in the cytoplasm, forms a multi-protein complex with an inhibitory subunit, IκBα. Upon activation by external stimuli, the inflammatory signals converge on a set of IκB kinases known as the IKK complex. The IKK complex phosphorylates two conserved N-terminal serine residues of IκBα, leading to its ubiquitination and degradation by the proteasome. The liberated NF-κB then enters the nucleus, interacts with κB elements in the promoter region of a variety of inflammatory response genes, and activates their transcription (Liu et al., "Nuclear Factor-κB Decoy: Infiltrating the Heart of the Matter in Inflammatory Heart Disease," *Circ Res* 89:850-2 (2001)). Thus, phosphorylation of IκBα appears to be the central point where diverse stimuli converge to regulate NF-κB.

Two IKKs, IKKα (IKK1) and IKKβ (IKK2), have been identified and shown to be part of the multi-protein IKK complex (Mercurio et al.; "IKK-1 and IKK-2: Cytokine-activated IκB Kinases Essential for NF-κB Activation," *Science* 278:860-6 (1997); Zandi et al., "The IκB Kinase Complex (IKK) Contains Two Kinase Subunits, IKKα and IKKβ, Necessary for IκB Phosphorylation and NF-κB Activation," *Cell* 91:243-52 (1997)). Both IKKα and IKKβ are Ser/Thr kinases, and each of them directly phosphorylates IκB proteins (Zandi et al., "Direct Phosphorylation of IκB by IKKα and IKKβ: Discrimination Between Free and NF-κB-bound Substrate," *Science* 281:1360-3 (1998); Lee et al., "MEKK1 Activates both IκB Kinase alpha and IκB Kinase beta," *Proc Natl Acad Sci USA* 95:9319-24 (1998)). Several other molecules in the IKK complex have also been identified, such as signal-regulated kinase (ERK) kinase 1 (MEKK1), NF-κB-inducing kinase (NIK), NF-κB essential modulator NEMO/IKKAP1/IKKγ, and IKK complex associated protein (Lee et al., "MEKK1 Activates both IκB Kinase alpha and IκB Kinase beta," *Proc Natl Acad Sci USA* 95:9319-24 (1998); Yamaoka et al., "Complementation Cloning of NEMO, a Component of the IκB Kinase Complex Essential for NF-κB Activation," *Cell* 93:1231-40 (1998); Rothwarf et al., "IKK-gamma is an Essential Regulatory Subunit of the IκB Kinase Complex," *Nature* 395: 297-300 (1998); Mercurio et al., "IκB kinase (IKK)-associated Protein 1, a Common Component of the Heterogeneous IKK Complex," *Mol Cell Biol* 19:1526-38 (1999)). These molecules have been shown to be essential for transmitting upstream signals to IKKα and IKKβ by acting as a kinase, regulatory protein, or scaffold protein. Thus, it would be desirable to identify which of these targets can be used to modulate inflammation, and particularly agents that can be used for therapeutic modulation of these targets to treat or prevent inflammatory conditions.

The present invention is directed to overcoming these and other deficiencies in the art.

SUMMARY OF THE INVENTION

A first aspect of the present invention relates to a method of treating or preventing an inflammatory condition that includes administering vincamine or a vincamine derivative to a patient under conditions effective to treat or prevent an inflammatory condition.

Preferably, when the vincamine derivative is vinpocetine, vinpocetine is either administered alone or in combination with another agent that is not a COX-2 inhibitor; and the inflammatory condition to be treated does not involve a gastrointestinal inflammatory condition.

A second aspect of the present invention relates to a pharmaceutical composition that includes vincamine or a vincamine derivative, and one or more of a steroid, angiotensin II receptor (type 1) antagonist, an angiotensin-converting enzyme (ACE) inhibitor, and a non-steroidal anti-inflammatory compound.

The data presented herein shows for the first time that the vincamine derivative vinpocetine acts in vitro and in vivo to inhibit NF-κB-dependent inflammatory response by targeting IKK. Vinpocetine inhibits TNFα-induced NF-κB activation and the subsequent induction of pro-inflammatory mediators in a variety of cell types. Vinpocetine also inhibits monocyte adhesion and chemotaxis. Moreover, vinpocetine potently inhibited TNFα- or LPS-induced inflammatory response in the lungs of mouse. The IKK-targeted activity of vinpocetine was also shown to be independent of its well-known inhibitory effect on Phosphodiesterase 1 (PDE1) activity and $Ca^{2+}/Na^+$ regulation. The present invention identifies vinpocetine and other vincamine derivatives as novel anti-inflammatory agents that act via disruption of the IKK pathway, which affords a novel therapeutic strategy for the treatment of various NF-κB-dependent inflammatory diseases or conditions. Based on these results, it is expected that vincamine and other vincamine derivatives that can induce IKK inhibition will similarly be useful.

BRIEF DESCRIPTION OF THE DRAWINGS

FIG. 5A illustrates microscopic images showing U937 monocytes adhering to HUVECs as assessed by in vitro adhesion assay. HUVECs were pretreatment with vehicle (DMSO), or 50 μM vinpocetine for 30 min exposed to TNFα (10 ng/ml) or vehicle for 6 hours. U937 monocyte adhesion on TNFα- or vehicle-stimulated HUVECs was analyzed. FIG. 5B shows quantitative monocyte adhesion to HUVECs. FIG. 5C shows monocyte chemotaxis to VSMCs measured by transwell migration. Rat aortic VSMCs were treated with or without TNFα (10 ng/ml) for 9 hours in the presence or absence of various doses of vinpocetine. VSMC-conditional medium was collected and used for monocyte chemotaxis assays in Boyden Chambers. Data represent means±SD of at least three independent experiments and each experiment was performed in triplicate. p<0.05 vs. control and #p<0.05 vs. TNFα alone.

FIG. 6A shows that intraperitoneal (i.p.) administration of vinpocetine (2.5, 5, and 10 mg/kg body weight) significantly inhibited induction of TNFα, IL-1 and MIP-2 mRNA in the lungs of mice by intratracheal (i.t.) administration of LPS (2 μg/mouse). FIG. 6B shows that vinpocetine (10 mg/kg body weight) inhibited polymorphonuclear neutrophil (PMN) infiltration in broncho-alveolar lavage (BAL) fluids from the lungs of mice treated with LPS. Data represent means±SD of at least three independent experiments. *P<0.05 vs. untreated group. #P<0.05 vs. LPS alone.

FIG. 7A shows that intraperitoneal (i.p.) administration of vinpocetine injection solution (10 mg/kg body weight) significantly inhibited induction of TNFα, IL-1b and MIP-2 mRNA in the lungs of mice by intratracheal (i.t.) administration of LPS (2 μg/mouse). FIG. 7B-C show that vinpocetine inhibited polymorphonuclear neutrophil (PMN) infiltration in broncho-alveolar lavage (BAL) fluids from the lungs of mice treated with LPS. Data represent means±SD of at least three independent experiments. *P<0.05 vs. untreated group. #P<0.05 vs. LPS alone.

FIG. 8A shows the effects of vinpocetine on TNFα-induced IκBα phosphorylation and degradation. Rat aortic VSMCs were treated with TNFα (10 ng/ml) for different time periods (0-30 minutes) as indicated in the presence or absence of vinpocetine (50 M). Western Blotting analysis was carried out to evaluate the levels of phosphorylated IκBα, total IκBα- and β-actin. FIG. 8B shows TNFα (10 ng/ml) induces IKK kinase activity in rat aortic VSMCs. IKK kinase activity was analyzed by an immune complex kinase assay. FIG. 8C shows that vinpocetine inhibits TNFα-induced IKK kinase activity. VSMCs were treated with TNFα for 10 min in the presence of various doses of vinpocetine as indicated. FIG.

8D illustrates the relative IKK activity as indicated. Intensities of the GST-IκBα bands in the autoradiogram were measured by densitometric scanning. Results were normalized to the control ([vinpocetine]=0) that is arbitrarily set to 100%. *p<0.05, **p<0.01 vs. vitipocetine at zero. FIGS. 8E-H illustrate the effects of vinpocetine on NF-κB activation induced by expressing constitutive active form of either MEKK1 (CA-MEKK1) (FIG. 8E), IKKα (CA-IKKα) (FIG. 8F), IKKβ (CA-IKKβ) (FIG. 8G), or WT p65 (FIG. 8H) in VSMCs. Data represent means±SD of at least three independent experiments. *p<0.05 vs. vector control group. #p<0.05 vs. either CA-MEKK1, CA-IKKα, CA-IKKβ, or WT p65 alone.

FIG. 9A is a representative autoradiogram showing IKK kinase activity (top) and Western blot analysis showing IKKβ levels (bottom). FIG. 9B shows the relative IKK activity as indicated. Intensities of the GST-IκBα bands in the autoradiogram were measured by densitometric scanning. Results were normalized to the control ([vinpocetine]=0) that is arbitrarily set to 100%. Data represent mean±SD from three independent experiments. *p<0.05 vs. vinpocetine at zero.

DETAILED DESCRIPTION OF THE INVENTION

Figure 1A:
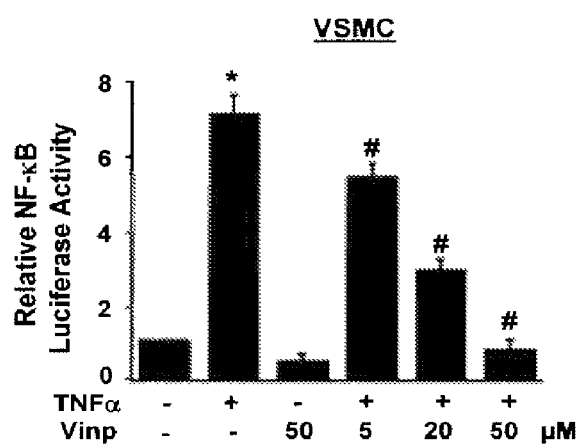
FIGS. 1A-D show that vinpocetine inhibits TNFα-induced NF-κB-dependent promoter activity in a variety of cell types. Rat aortic VSMCs (FIG. 1A) or Vascular ECs (HUVECs) (FIG. 1B), Lung epithelial cell A549 (FIG. 1C) and macrophage RAW264.7 (FIG. 1D) transfected with NF-κB-Luc reporter plasmid were stimulated with or without TNFα (10 ng/ml) for 6 hours in the presence or absence of various doses of vinpocetine (Vinp) as indicated (FIG. 1A) or 50 μM vinpocetine (FIGS. 1B-D)). Cells were then lysed for luciferase assay. Data represent means±SD of at least three independent experiments and each experiment was performed in triplicate. *P<0.05 vs. control and #P<0.05 vs. TNFα alone.

The present invention relates to methods of treating or preventing an inflammatory condition that include the administering of vincamine or a vincamine derivative to a patient under conditions effective to treat or prevent the inflammatory condition. Pharmaceutical compositions that can be used in the method of the present invention are also disclosed herein.

As used herein, the patient can be any mammal, but preferably the mammal is a human, a non-human primate, a rodent, a cow, a horse, a sheep, or a pig. Other mammals can also be treated in accordance with the present invention.

As used herein, the vincamine derivative can be any known or hereafter developed derivative of vincamine that can induce IKK inhibition. The induced IKK inhibition can be caused either directly or indirectly by the vincamine derivative. By directly, it is intended that administered derivative acts on IKK itself, whereas by indirectly it is intended that either a metabolite of the derivative antagonizes IKK, or a native cellular component acted upon by the derivative (or its metabolite) antagonizes IKK. Thus, through the induced inhibition of IKK, vincamine or vincamine derivatives can be used to treat inflammatory conditions that are mediated via NF-κB.

Vincamine has the structure

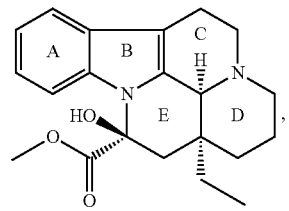

and its recovery from the leaves of *Vinca minor* L. is well known in the art. A number of vincamine derivatives have been synthesized and are well tolerated for therapeutic administration. A number of known vincamine derivatives are identified in PubChem Substance database of the National Center for Biotechnology Information. These include, without limitation, derivatives of the ester sidechain, derivatives of the A ring to include one or more halo, hydroxyl, or alkyl substituents, derivatives of the C ring to include a keto or hydroxyl substituent, derivatives of the D ring to include one or more hydroxyl or alkyl substituents with or without unsaturation of the D ring, and unsaturation of the E ring.

Preferred vincamine derivatives are those that share an ability to directly or indirectly induce inhibition of (i.e., antagonize) IKK. Antagonists of IKK can be measured in vitro via IKK kinase assay as described in the accompanying examples and elsewhere (see Shishodia et al., "Ursolic Acid Inhibits Nuclear Factor-κB Activation Induced by Carcinogenic Agents through Suppression of IκBα kinase and p65 Phosphorylation: Correlation with Down-regulation of Cyclooxygenase 2, Matrix Metalloproteinase 9, and Cyclin D1," *Cancer Res.* 63(15):4375-83 (2003), which is hereby incorporated by reference in its entirety. The ability of vincamine derivatives to indirectly antagonize IKK can be assessed by recovering cell lysates (following uptake of the vincamine derivative) and assessing the ability of the cell lysates to antagonize IKK; the cell lysates contain a metabolite of the vincamine derivative or a native cellular component acted upon by vincamine derivative or its metabolite, which native cellular component—when acted upon—inhibits IKK.

Exemplary vincamine derivatives include, without limitation:

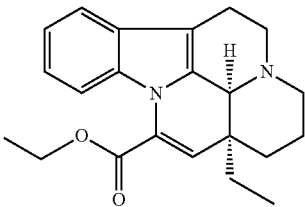

(+)-vinpocetine or salts thereof;

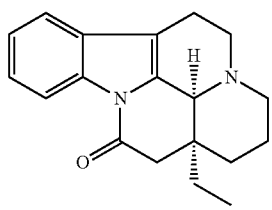

(−)-eburnamenine (also known as vinburnine) or salts thereof;

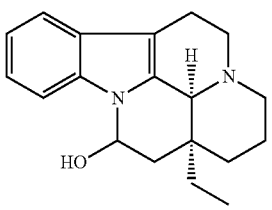

eburnamenine or salts thereof;

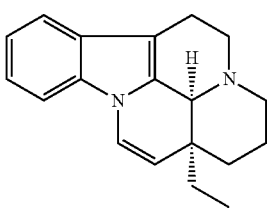

eburnamenine or salts thereof;

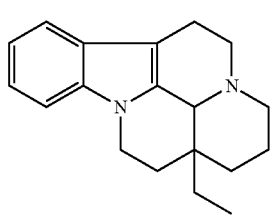

dihydro-eburnamenine or salts thereof;

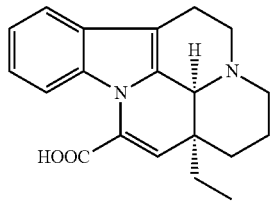

apovincaminic acid or salts thereof;

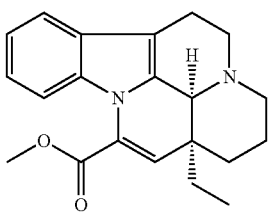

apovincamine or salts thereof;

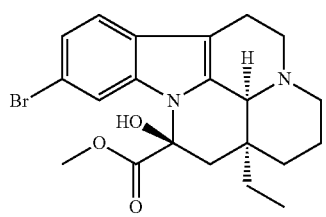

brovincamine or salts thereof;

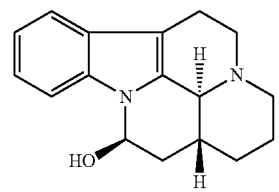

vindeburnol (also known as RU-24722) or salts thereof;

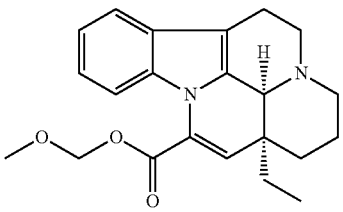

methylenemethoxyapovincaminate (also known as MR-711) or salts thereof;

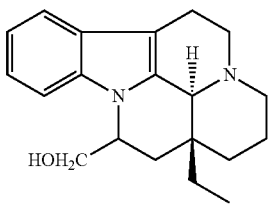

(3S,16R)-didydro-eburnamenine-4-methanol (also known as RGH-0537) or salts thereof;

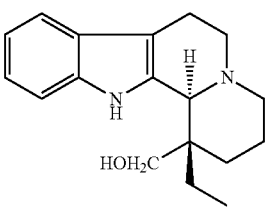

(1S,12S)-indoloquinolizinyl-1-methanol (also known as RGH-2981 or vintoperol) or salts thereof;

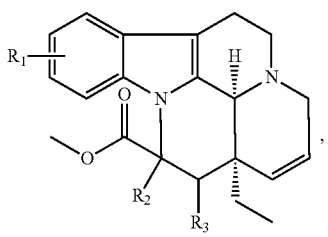

where $R_1$ is a halogen, $R_2$ can be a hydroxy group whereas $R_3$ can be hydrogen, or $R_2$ and $R_3$ together form an additional bond between the carbon atoms which carry them, or salts thereof (as described in U.S. Pat. No. 4,285,949 to Hannart, which is hereby incorporated by reference in its entirety);

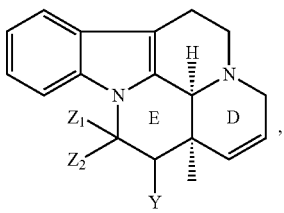

where the compound is formed by a cis-fusion of the D/E rings, and either (i) Y is hydrogen, in which case $Z_1$ and $Z_2$ together represent simultaneously an oxygen atom or $Z_1$ is a methoxycarbonyl radical and $Z_2$ is a hydroxy radical, or (ii) where Y and $Z_2$ together form a carbon-carbon bond and $Z_1$ is a methoxycarbonyl radical, or salts thereof (as described in U.S. Pat. No. 4,033,969 to Sevenét et al., which is hereby incorporated by reference in its entirety);

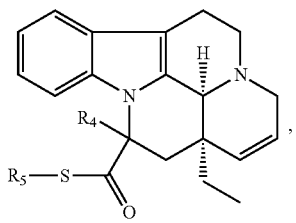

where $R_4$ is hydrogen or a hydroxyl group, and $R_5$ is an alkyl group, or salts thereof (as described in U.S. Pat. No. 4,364,947 to Toyomaki et al., which is hereby incorporated by reference in its entirety);

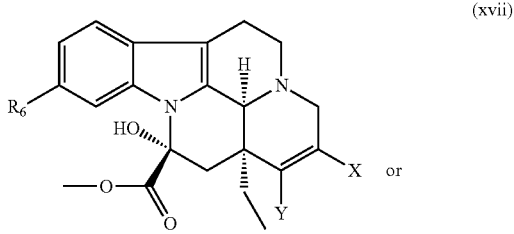

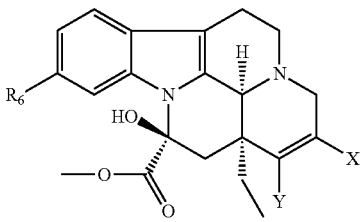

where $R_6$ is hydrogen or methoxy, X and Y are hydrogen or are together are a double bond between the ring carbon atoms to which they are bonded, or salts thereof (as described in U.S. Pat. No. 4,145,552 to Heymès, which is hereby incorporated by reference in its entirety); and (xviii) combinations of any two or more of the above compounds or salts thereof.

The vincamine derivatives can also be in the form of a salt, preferably a pharmaceutically acceptable salt. The term "pharmaceutically acceptable salt" refers to those salts that retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxylic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcysteine and the like. Other salts are known to those of skill in the art and can readily be adapted for use in accordance with the present invention.

The term "vincamine derivative" is also intended to encompass prodrugs of vincamine or its derivative compounds. A "prodrug" refers to an agent that is converted into the parent drug in vivo. Prodrugs are often useful because, in some situations, they may be easier to administer than the parent drug. They may, for instance, be bioavailable by oral administration whereas the parent is not. The prodrug may also have improved solubility in pharmaceutical compositions over the parent drug, or may demonstrate increased palatability or be easier to formulate. An example, without limitation, of a prodrug would be a compound of the present invention which is administered as an ester (the "prodrug") to facilitate transmittal across a cell membrane where water solubility is detrimental to mobility but which then is metabolically hydrolyzed to the active entity, such as a carboxylic acid derivative, once inside the cell where water-solubility is beneficial. A further example of a prodrug might be a short peptide (polyaminoacid) bonded to an acid group where the peptide is metabolized to provide the active moiety.

The term "vincamine derivative" is also intended to encompass any active metabolites of these compounds. For instance, as demonstrated in the accompanying examples, vinpocetine itself does not block IKK activity; whereas cell lysates from cells treated with vinpocetine do block IKK activity. The cell lysates are believed to contain a vinpocetine metabolite that possesses the requisite activity.

It should also be appreciated that other vincamine derivatives can also be used in accordance with the present invention.

Depending upon the site of inflammation, it maybe desirable to utilize peripherally active vincamine derivatives such as RGH-0537 and RGH-2981, both identified above. In another embodiment, those vincamine derivatives capable of crossing the blood-brain barrier can be used, such as vinpocetine.

According to one embodiment, the vincamine derivative is vinpocetine, but the vinpocetine is not used in combination with any other therapeutic agents (described infra). Vinpocetine is produced by slightly altering the vincamine molecule, an alkaloid extracted from the Periwinkle plant, Yinca minor. Vinpocetine was originally discovered and marketed in 1978 under the trade name Vavinton (Hungary). Since then, vinpocetine has been widely used in many countries for preventative treatment of cerebrovascular disorder and cognitive impairment including stroke, senile dementia, and memory disturbances due to the beneficial cerebrovascular effect and neuroprotective profile (Bönöezk et al., "Role of Sodium Channel Inhibition in Neuroprotection: Effect of Vinpocetine," *Brain Res Bull* 53:245-54 (2000), each of which is hereby incorporated by reference in its entirety). For instance, different types of vinpocetine-containing memory enhancer (named Intelectol® in Europe, and Memolead® in Japan) have been currently used as a dietary supplement worldwide. Vinpocetine is a cerebral vasodilator that improves brain blood flow (Bönöezk et al., "Role of Sodium Channel Inhibition in Neuroprotection: Effect of Vinpocetine," *Brain Res Bull* 53:245-54 (2000), each of which is hereby incorporated by reference in its entirety). Vinpocetine has also been shown to act as a cerebral metabolic enhancer by enhancing oxygen and glucose uptake from blood and increasing neuronal ATP bioenergy production (Bönöezk et al., "Role of Sodium Channel Inhibition in Neuroprotection: Effect of Vinpocetine," *Brain Res Bull* 53:245-54 (2000), each of which is hereby incorporated by reference in its entirety). Vinpocetine appears to have multiple cellular targets such as $Ca^{2+}$/Calmodulin-stimulated phosphodiesterases (PDE1), voltage-dependent $Na^+$-channels and $Ca^{2+}$-channels (Bönöezk et al., "Role of Sodium Channel Inhibition in Neuroprotection: Effect of vinpocetine," *Brain Res Bull* 53:245-54 (2000), each of which is hereby incorporated by reference in its entirety). To date, there have been no reports of significant side effects, toxicity or contraindications at the therapeutic doses (Balestreri et al., "A Double-blind Placebo Controlled Evaluation of the Safety and Efficacy of vinpocetine in the Treatment of Patients with Chronic Vascular Senile Cerebral Dysfunction," *J Am Geriatr Soc* 35:425-30 (1987), which is hereby incorporated by reference in its entirety).

According to a further embodiment, the vincamine derivative is vinpocetine, which is used in combination with an effective amount another agent that can be used to treat the inflammation, where such agent is not a COX-2 inhibitor. Exemplary agents are identified hereinafter.

According to another embodiment, the vincamine derivative is a vincamine derivative other than vinpocetine. Many of the other vincamine derivatives identified above have also been identified as vasodilators (Vas et al., "Eburnamine Derivatives and the Brain," *Med Res Rev.* 25(6):737-57 (2005), which is hereby incorporated by reference in its entirety). The use of vincamine derivatives other than vinpocetine in combination with an effective amount of another agent that can be used to treat the inflammation is also contemplated. Exemplary agents are identified hereinafter.

The present invention encompasses administration of vincamine or the vincamine derivatives prior to the onset of inflammation as a preventative (e.g., prior to surgical trauma) or after onset of an inflammatory condition as a therapeutic. For purposes of controlling inflammation, it is preferable to administer the vincamine derivative soon after onset of the inflammatory condition. Chronic inflammatory conditions may be treated repeatedly. It is therefore contemplated that the administration of the vincamine or vincamine derivative can be used to reduce inflammation at an anatomical site, and thereby control symptoms associated with inflammation such as pain. By treating or preventing inflammation, it is intended that the degree (i.e., severity) of inflammation can be reduced (as compared to the absence of treatment) or that the longevity of the inflammatory response can be shortened.

Exemplary modes of administration include, without limitation, orally, by inhalation, by intranasal or airway instillation, optically, intranasally, by middle ear injection, by ear drops, topically, transdermally, parenterally, subcutaneously, intravenous injection, intra-arterial injection, injection to a site of inflammation, intradermal injection, intramuscular injection, intrapleural instillation, intraperitoneally injection, intraventricularly, intralesionally, by application to mucous membranes, or implantation of a sustained release vehicle.

The inflammatory condition can be any inflammatory condition that is mediated via NF-κB. Exemplary inflammatory conditions include, without limitation, atherosclerosis, acute and chronic lung inflammation (e.g., chronic bronchitis, asthma, lung infection including bacterial and viral infections such as SARS and influenza, cystic fibrosis, etc.), inflammation of virus-infected tissues (e.g., viral lung infections, viral myocarditis, viral meningitis, etc.), ulcerative colitis, endotoxic shock, arthritis (e.g, rheumatoid arthritis, juvenile arthritis, osteoarthritis, psoriatic arthritis, reactive arthritis, viral or post-viral arthritis, ankylosing spondylarthritis, etc.), psoriasis, Crohn's disease, inflammatory bowel disease, insulin dependent diabetes mellitus, injury independent type II diabetes, ischemia induced inflammation, otitis media (middle ear infection), gout, multiple sclerosis, cachexia, and Ataxia Telangiestasia. The administration of vincamine or vincamine derivatives to treat other NF-κB-mediated inflammatory conditions is also contemplated.

When the vincamine derivative is vinpocetine, the inflammatory condition to be treated preferably is not a gastrointestinal inflammatory condition, such as ulcerative colitis, Crohn's disease, inflammatory bowel disease.

As noted above, vincamine or vincamine derivatives can also be administered in combination with one or more other therapeutic agents, including steroids, preferably corticosteroids, angiotensin II receptor (type 1) antagonists, angiotensin-converting enzyme (ACE) inhibitors, and non-steroidal anti-inflammatory drugs (NSAIDs). As noted above, the use of NSAIDs—known as COX-2 inhibitors—in combination with vinpocetine is explicitly excluded.

The mechanism of action for ACE inhibitors is via an inhibition of angiotensin-converting enzyme (ACE) that prevents conversion of angiotensin I to angiotensin II, a potent vasoconstrictor, resulting in lower levels of angiotensin II, which causes a consequent increase in plasma renin activity and a reduction in aldosterone secretion. Angiotensin Receptor Blockers (ARBs) work as their name implies by directly blocking angiotensin II receptors and thus preventing the action of angiotensin II.

The term ACE inhibitor is intended to embrace any agent or compound, or a combination of two or more agents or compounds, having the ability to block, partially or completely, the rapid enzymatic conversion of the physiologically inactive decapeptide form of angiotensin ("Angiotensin I") to the vasoconstrictive octapeptide form of angiotensin ("Angiotensin II").

Examples of suitable ACE inhibitors include, without limitation, the following compounds: AB-103, ancovenin, benazeprilat, BRL-36378, BW-A575C, CGS-13928C, CL242817, CV-5975, Equaten, EU4865, EU-4867, EU-5476, foroxymithine, FPL 66564, FR-900456, Hoe-065, 15B2, indolapril, ketomethylureas, KRI-1177, KR1-1230, L681176, libenzapril, MCD, MDL-27088, MDL-27467A, moveltipril, MS41, nicotianamine, pentopril, phenacein, pivopril, rentiapril, RG-5975, RG-6134, RG-6207, RGH0399, ROO-911, RS-10085-197, RS-2039, RS 5139, RS 86127, RU-44403, S-8308, SA-291, spiraprilat, SQ26900, SQ-28084, SQ-28370, SQ-28940, SQ-31440, Synecor, utibapril, WF-10129, Wy-44221, Wy-44655, Y-23785, Yissum, P-0154, zabicipril, Asahi Brewery AB-47, alatriopril, BMS 182657, Asahi Chemical C-111, Asahi Chemical C-112, Dainippon DU-1777, mixanpril, Prentyl, zofenoprilat, I (-I-carboxy-6-(4-piperidinyl)hexyl)amino]-1-oxo-propyl octahydro-1H-indole-2-carboxylic acid, Bioproject BP1137, Chiesi CHF 1514, Fisons FPL-66564, idrapril, perindoprilat and Servier S-5590, alacepril, benazepril, captopril, cilazapril, delapril, enalapril, enalaprilat, fosinopril, fosinoprilat, imidapril, lisinopril, perindopril, quinapril, ramipril, ramiprilat, saralasin acetate, temocapril, tranolapril, trandolaprilat, ceranapril, moexipril, quinaprilat spirapril, and combinations thereof.

The phrase "ACE inhibitor" also embraces so-called NEP/ACE inhibitors (also referred to as selective or dual acting neutral endopeptidase inhibitors) which possess neutral endopeptidase (NEP) inhibitory activity and angiotensin converting enzyme (ACE) inhibitory activity. Examples of NEP/ACE inhibitors particularly preferred and suitable for use herein are those disclosed in U.S. Pat. Nos. 5,508,272, 5,362,727, 5,366,973, 5,430,145, 5,225,401, 4,722,810, 5,223,516, 5,508,272, 5,552,397, 4,749,688, 5,504,080, 5,612,359, 5,525,723, 5,430,145, and 5,679,671, and European Patent Applications 0481522, 0534263, 0534396, 0534492, and 0671172, each of which is hereby incorporated by reference in its entirety.

The term "angiotensin II receptor (type 1) antagonist" is intended to embrace any agent or compound, or a combination of two or more agents or compounds, having the ability to block, partially or completely the binding of angiotensin II at angiotensin receptors, specifically at the $AT_1$ receptor. These agents are also known as Angiotension Receptor Blockers (ARBs).

Examples of suitable angiotensin II antagonists include, without limitation, the following compounds: saralasin acetate, candesartan cilexetil, CGP-63170, EMD-66397, KT3-671, LR-B/081, valsartan, A-81282, BIBR-363, BIBS-222, BMS-184698, candesartan, CV-11194, EXP-3174, KW-3433, L-161177, L-162154, LR-B/057, LY-235656, PD-150304, U-96849, U-97018, UP-275-22, WAY-126227, WK-1492.2K, YM-31472, losartan potassium, E-4177, EMD-73495, eprosartan, HN-65021, irbesartan, L-159282, ME-3221, SL-91.0102, Tasosartan, Telmisartan, UP-269-6, YM-358, CGP-49870, GA-0056, L-159689, L-162234, L-162441, L-163007, PD-123177, A-81988, BMS-180560, CGP-38560A, CGP48369, DA-2079, DE-3489, DuP-167, EXP-063, EXP-6155, EXP-6803, EXP-7711, EXP-9270, FK-739, HR-720, ICI-D6888, ICI-D7155, ICI-D8731, isoteoline, KIL-1177, L-158809, L-158978, L-159874, LRB087, LY-285434, LY-302289, LY-315995, RG-13647, RWJ-38970, RWJ-46458, S-8307, S-8308, saprisartan, saralasin, sarmesin, WK-1360, X-6803, ZD-6888, ZD-7155, ZD-8731, BIBS39, C1-996, DMP-811, DuP-532, EXP-929, L-163017, LY-301875, XH-148, XR-510, zolasartan, PD-123319, and combinations thereof.

Exemplary corticosteroids include, without limitation, triamcinolone, fluocinolone, cortisone, hydrocortisone, ciclesonide, fluticasone, flunisolide, mometasone, betamethasone, depomedrol, dexamethasone, budesonide, beclomethasone, prednisone, methylprednisolone, prednisolone, and combinations thereof.

Exemplary NSAIDs include, without limitation, ibuprofen (2-(isobutylphenyl)-propionic acid); methotrexate (N-[4-(2,4 diamino 6-pteridinyl-methyl]methylamino]benzoyl)-L-glutamic acid); aspirin (acetylsalicylic acid); salicylic acid; diphenhydramine (2-(diphenylmethoxy)-NN-dimethylethylamine hydrochloride); naproxen (2-naphthaleneacetic acid, 6-methoxy-9-methyl-, sodium salt, (−)); ketorolac (1H-Pyrrolizine-1-carboxylic acid, 2,3-dihydro-5-benzoyl-, (+−)); phenylbutazone (4-butyl-1,2-diphenyl-3,5-pyrazolidinedione); sulindac-(2)-5-fluoro-2-methyl-1-[[p-(methylsulfinyl)phenyl]methylene-]-1H-indene-3-acetic acid; diflunisal (2',4'-difluoro-4-hydroxy-3-biphenylcarboxylic acid; piroxicam (4-hydroxy-2-methyl-N-2-pyridinyl-2H-1,2-benzothiazine-2-carboxamide 1,1-dioxide, an oxicam; indomethacin (1-(4-chlorobenzoyl)-5-methoxy-2-methyl-1H-indole-3-acetic acid); meclofenamate sodium (N-(2,6-dichloro-m-tolyl)anthranilic acid, sodium salt, monohydrate); ketoprofen (2-(3-benzoylphenyl)-propionic acid; tolmetin sodium (sodium 1-methyl-5-(4-methylbenzoyl-1H-pyrrole-2-acetate dihydrate); diclofenac sodium (2-[(2,6-dichlorophenyl)amino]benzeneatic acid, monosodium salt); hydroxychloroquine sulphate (2-{[4-[(7-chloro-4-quinolyl)amino]pentyl]ethylamino}ethanol sulfate (1:1); penicillamine (3-mercapto-D-valine); flurbiprofen ([1,1-biphenyl]-4-acetic acid, 2-fluoro-alphamethyl-, (+−)); cetodolac (1-8-diethyl-13,4,9, tetra hydropyrano-[3-4-13]indole-1-acetic acid; mefenamic acid (N-(2,3-xylyl)anthranilic acid; and diphenhydramine hydrochloride (2-diphenyl methoxy-N,N-di-methylethamine hydrochloride).

These additional therapeutic agents can be co-administered either in a single formulation or separately as multiple doses. Administration is preferably carried out directly to a site or adjacent to a site of inflammation, although systemic administration routes are also contemplated. Suitable modes of administration include those identified above.

These active agents are preferably administered in the form of pharmaceutical formulations that include one or more vincamine derivatives (or vincamine itself), alone or in combination with one or more additional active agents, together with a pharmaceutically acceptable carrier. The term "pharmaceutically acceptable carrier" refers to any suitable adjuvants, carriers, excipients, or stabilizers, and can be in solid or liquid form such as, tablets, capsules, powders, solutions, suspensions, or emulsions.

Typically, the composition will contain from about 0.01 to 99 percent, preferably from about 20 to 75 percent of active compound(s), together with the adjuvants, carriers and/or excipients.

For example, application to mucous membranes can be achieved with an aerosol spray containing small particles of the active agent(s) in a spray or dry powder form.

The solid unit dosage forms can be of the conventional type. The solid form can be a capsule and the like, such as an ordinary gelatin type containing the compounds of the present invention and a carrier, for example, lubricants and inert fillers such as, lactose, sucrose, or cornstarch. In another embodiment, these compounds are tableted with conventional tablet bases such as lactose, sucrose, or cornstarch in combination with binders like acacia, cornstarch, or gelatin, disintegrating agents, such as cornstarch, potato starch, or alginic acid, and a lubricant, like stearic acid or magnesium stearate.

The tablets, capsules, and the like can also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, or saccharin. When the dosage unit form is a capsule, it can contain, in addition to materials of the above type, a liquid carrier such as a fatty oil.

Various other materials may be present as coatings or to modify the physical form of the dosage unit. For instance, tablets can be coated with shellac, sugar, or both. A syrup can contain, in addition to active ingredient, sucrose as a sweetening agent, methyl and propylparabens as preservatives, a dye, and flavoring such as cherry or orange flavor.

The active agent(s) may also be administered in injectable dosages by solution or suspension of these materials in a physiologically acceptable diluent with a pharmaceutical adjuvant, carrier or excipient. Such adjuvants, carriers and/or excipients include, but are not limited to, sterile liquids, such as water and oils, with or without the addition of a surfactant and other pharmaceutically and physiologically acceptable components. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

These active compounds may also be administered parenterally. Solutions or suspensions of these active compounds can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

Preferred pharmaceutical compositions include, without limitation, (1) a vincamine derivative in combination with a corticosteroid, in a pharmaceutically acceptable vehicle; (2) a vincamine derivative in combination with an angiotensin II receptor antagonist, in a pharmaceutically acceptable vehicle; (3) a vincamine derivative in combination with an ACE inhibitor, in a pharmaceutically acceptable vehicle; (4) a vincamine derivative other than vinpocetine in combination with an NSAID, in a pharmaceutically acceptable vehicle; (5) a vincamine derivative in combination with a corticosteroid and an NSAID, in a pharmaceutically acceptable vehicle; and (6) a vincamine derivative in combination with a corticosteroid and one or both of an angiotensin II receptor antagonist and an ACE inhibitor, in a pharmaceutically acceptable vehicle.

According to one embodiment, for use in treating or preventing inflammation of the lungs, the pharmaceutical composition is in the form of a lung surfactant formulation or an inhalable formulation (either powder or nebulized fluid).

Examples of suitable surfactant formulations that can be modified to include vincamine or the vincamine derivative include, without limitation, exogenous lung surfactant formulations (e.g., Infasurf® (Forest Laboratories), Survanta® (Ross Products), and Curosurf® (DEY, California, USA)) and synthetic lung surfactant formulations (e.g., Exosurf® (GlaxoWellcome Inc.) and ALEC). These surfactant formulations are typically administered via airway instillation (i.e., after intubation) or intratracheally.

According to another embodiment, for use in treating or preventing inflammation caused by an arthritic condition or joint inflammation, the pharmaceutical composition is in the form of an injectable formulation, a transdermal formulation, or topical formulation.

Transdermal formulations include, without limitation, a transdermal delivery system, typically in the form of a patch that contains a depot of the active drug(s) in a pharmaceutically acceptable transdermal carrier, or simply a solution phase carrier that is deposited onto the skin, where it is absorbed. A number of transdermal delivery systems are known in the art, such as U.S. Pat. No. 6,149,935 to Chiang et al., PCT Application Publ. No. WO2006091297 to Mitragotri et al., EP Patent Application EP1674068 to Reed et al., PCT Application Publ. No. WO2006044206 to Kanios et al., PCT Application Publ. No. WO2006015299 to Santini et al., each of which is hereby incorporated by reference in its entirety.

Topical formulations include, without limitation, gels, pastes, creams, lotions, ointments, sprays, powders, oils, and solutions. The composition may optionally be delivered via a liposome, nanosome, or mycel. The topical delivery vehicle may also include one or more other topically acceptable additives known in the art.

A cream is a formulation that contains water and oil and is stabilized with an emulsifier. Lipophilic creams are called water-in-oil emulsions, and hydrophilic creams oil-in-water emulsions. The cream base for water-in-oil emulsions are normally absorption bases such as vaseline, ceresin or lanolin. The bases for oil-in-water emulsions are generally mono-, di- and triglycerides of fatty acids or fatty alcohols with soaps, alkyl sulfates or alkyl polyglycol ethers as emulsifiers.

A lotion is an opaque, thin, non-greasy emulsion liquid dosage form for external application to the skin, which generally contains a water-based vehicle with greater than 50% of volatiles and sufficiently low viscosity that it may be delivered by pouring. Lotions are usually hydrophilic, and contain greater than 50% of volatiles as measured by LOD (loss on drying). A lotion tends to evaporate rapidly with a cooling sensation when rubbed onto the skin.

A paste is an opaque or translucent, viscous, greasy emulsion or suspension semisolid dosage form for external application to the skin, which generally contains greater than 50% of hydrocarbon-based or a polyethylene glycol-based vehicle and less than 20% of volatiles. A paste usually contains a large proportion (20-50%) of dispersed solids in a fatty or aqueous vehicle. An ointment tends not to evaporate or be absorbed when rubbed onto the skin.

An ointment is an opaque or translucent, viscous, greasy emulsion or suspension semisolid dosage form for external application to the skin, which generally contains greater than 50% of hydrocarbon-based or a polyethylene glycol-based vehicle and less than 20% of volatiles. An ointment is usually lipophilic, and contains >50% of hydrocarbons or polyethylene glycols as the vehicle and <20% of volatiles as measured by LOD. An ointment tends not to evaporate or be absorbed when rubbed onto the skin.

A gel is usually a translucent, non-greasy emulsion or suspension, semi-solid dosage form for external application to the skin, which contains a gelling agent in quantities sufficient to impart a three-dimensional, cross-linked matrix. A gel is usually hydrophilic, and contains sufficient quantities of a gelling agent such as starch, cellulose derivatives, carbomers, magnesium-aluminum silicates, xanthan gum, colloidal silica, and aluminum or zinc soaps.

In the case of a composition for topical administration, the composition may further include one or more drying agents, anti-foaming agents; buffers, neutralizing agents, agents to adjust pH; coloring agents; emollients; emulsifying agents, emulsion stabilizers and viscosity builders; humectants; odorants; preservatives, antioxidants, and chemical stabilizers; solvents; and thickening, stiffening, and suspending agents, and a balance of water or solvent.

According to a further embodiment, which is suitable for implantation, the pharmaceutical formulation may be in the form of a polymeric matrix in which the agents (vincamine or vincamine derivative) to be administered are captured. Release of the vincamine or vincamine derivative can be controlled via selection of materials and the amount of drug loaded into the vehicle. Implantable drug delivery systems include, without limitation, microspheres, hydrogels, polymeric reservoirs, cholesterol matrices, polymeric systems, and non-polymeric systems. A number of suitable implantable delivery systems are known in the art, such as U.S. Pat. No. 6,464,687 to Ishikawa et al., U.S. Pat. No. 6,074,673 to Guillen, each of which is hereby incorporated by reference in its entirety.

Preferred dosages of vincamine or the vincamine derivative are between about 0.01 to about 2 mg/kg, preferably 0.05 to about 1 mg/kg, most preferably about 0.05 to about 0.5 mg/kg. For example, vinpocetine is commercially available in 10 mg doses. Dosages for corticosteroids, ACE inhibitors, angiotensin II receptor antagonists, and NSAIDs are well known in the art. However, it is expected that the dosages of these other active agent(s) can, under certain circumstances, be reduced when co-administered with vincamine or the vincamine derivative.

EXAMPLES

The following examples are provided to illustrate embodiments of the present invention but they are by no means intended to limit its scope.

Materials and Methods for Examples

Reagents:

Vinpocetine as a compound was purchased from BIOMOL (PA, USA); Cavinton™ (injectable vinpocetine composition, 50 µM) was obtained from Gedeon Richter Co. (Hungary). Recombinant mouse TNFα was purchased from Roche (Mannheim, Germany). IC86340 (PDE1 inhibitor) was a gift from ICOS Inc. Polyclonal antibody against IκBα (sc-371) and actin (sc-1616) were purchased from Santa Cruz (CA, USA). Polyclonal antibody against phospho-Ser32 IκBα (#9241) was purchased from Cell Signaling (MA, USA). IKKα and IKKβ antibodies were purchased from Santa Cruz (CA, USA) and Cell Signaling (MA, USA), respectively.

Cell Culture:

Rat aortic vascular smooth muscle cells (VSMCs) were isolated from 250-300 g male Sprague-Dawley rats using enzymatic dissociation method and maintained in DMEM medium with 10% fetal bovine serum (FBS) (Life Technologies, Rockville, Md.) as described previously (Aizawa et al., "Role of Phosphodiesterase 3 in NO/cGMP-mediated Anti-inflammatory Effects in Vascular Smooth Muscle Cells," *Circ Res* 93:406-13 (2003), which is hereby incorporated by reference in its entirety). Cells at passages 5-10 were used for experiment. Human umbilical vein endothelial cells (HUVECs) were isolated from human umbilical veins and grown in Medium 200 with low serum growth supplement (Cascade Biologics, Inc., Portland, Oreg.) as described previously (Che et al., "Insulin-like Growth Factor-1 Enhances Inflammatory Responses in Endothelial Cells: Role of Gab1 and MEKK3 in TNF-α-induced c-Jun and NF-κB Activation and Adhesion Molecule Expression," *Circ Res* 90: 1222-30 (2002), which is hereby incorporated by reference in its entirety). Cells at passages 4 were used for experiments. Human lung epithelial cell line A549 were maintained in F-12K medium supplemented with 10% FBS as described previously (19). Macrophage-like cell line (U937) and monocyte cell line (THP1) were grown in RPMI 1640 medium supplemented with 10% FBS. Mouse macrophage cell line RAW 264.7 (American Type Culture Collection, Manassas, Va.) was cultured in DMEM supplemented with 10% FBS. All cells were cultured at under standard conditions (5% $CO_2$ in air in a humidified environment at 37° C.). Hela cells were maintained in minimal essential medium supplemented with 10% FBS as described previously (Shuto et al., "Activation of NF-κB by Nontypeable *Hemophilus influenzae* is Mediated by Toll-like Receptor 2-TAK1-dependent NIK-IKKα/β-IκBα and MKK3/6-p38 MAP Kinase Signaling Pathways in Epithelial cells," *Proc Natl Acad Sci USA* 98:8774-8779 (2001), which is hereby incorporated by reference in its entirety).

Western Blot Analysis:

Cells lysates were prepared in the buffer containing 20 mM Tris-HCl (pH8.0), 0.5 M NaCl, 0.25% Triton X-100, 1 mM EDTA, 1 mM EGTA, 10 mM-glycerophosphate, 10 mM NaF, 100 μM Na₃VO₄, 1 mM benzamidine, 2 μM PMSF, 1 mM DTT and protease inhibitor cocktail (Sigma, MO. USA), by scraping, sonication, and centrifugation at 12,000 g for 15 min. Supernatant were collected and then subjected to SDS-PAGE and Western blot analysis with indicated antibodies.

RNA isolation and real-time RT-PCR:

Total RNA was isolated with TRIzol reagent (Invitrogen) by following the manufacturer's instructions. For the reverse transcription reaction, TaqMan reverse transcription reagents (Applied Biosystems) were used. In brief, the reverse transcription reaction was performed for 60 min at 37° C., followed by 60 min at 42° C. by using oligo (dT) and random hexamers. PCR amplifications were performed by using SYBR Green Universal Master Mix. In brief, reactions were performed in duplicate containing 2× Universal Master Mix, 1 μl of template cDNA and 100 nM primers in a final volume of 12.5 μl, and they were analyzed in a 96-well optical reaction plate (Applied Biosystems). The relative quantities of mRNAs were obtained by using the comparative Ct method and were normalized with predeveloped Taqman assay reagent rat or mouse glyceraldehydes-3-phosphate dehydrogenase or human cyclophilin as an endogenous control (Applied Biosystems). The primer sequences are shown in Table I below.

TABLE 1

Primers Used for Real-time PCR Sequences

| | 5'-Primer | 3'-Primer | Accession No. |
|---|---|---|---|
| rTNFα | AGAACAGCAACTCCAGAACACCCT (SEQ ID NO: 1) | TGCCAGTTCCACATCTCGGATCAT (SEQ ID NO: 2) | NM_012675 |
| rIL-1β | ACCTGCTAGTGTGTGATGTTCCCA (SEQ ID NO: 3) | AGGTGGAGAGCTTTCAGCTCACAT (SEQ ID NO: 4) | NM_031512 |
| rCINC-1 | AGACAGTGGCAGGGATTCACTTCA (SEQ ID NO: 5) | TGTGGCTATGACTTCGGTTTGGGT (SEQ ID NO: 6) | NM_030845 |
| rMCP-1 | TGCTGTCTCAGCCAGATGCAGTTA (SEQ ID NO: 7) | TACAGCTTCTTTGGGACACCTGCT (SEQ ID NO: 8) | NM_031530 |
| rVACM-1 | ACTGTCAACTGCACGGTCCCTAAT (SEQ ID NO: 9) | ACAAGAGCTTTCCCGGTGTCTTCA (SEQ ID NO: 10) | NM_012889 |
| rGAPDH | ACAAGATGGTGAAGGTCGGTGTGA (SEQ ID NO: 11) | AGCTTCCCATTCTCAGCCTTGACT (SEQ ID NO: 12) | AF106860 |
| hTNFα | CAGAGGGAAGAGTTCCCCAG (SEQ ID NO: 13) | CCTTGGTCTGGTAGGAGACG (SEQ ID NO: 14) | NM_000594 |
| hIL-1β | AAACAGATGAAGTGCTCCTTCCAGG (SEQ ID NO: 15) | TGGAGAACACCACTTGTTGCTCCA (SEQ ID NO: 16) | NM_000576 |
| hIL-8 | AACATGACTTCCAAGCTGGCC (SEQ ED NO: 17) | TTATGAATTCTCAGCCCTCTTC (SEQ ID NO: 18) | NM_000584 |
| hMCP-1 | CCCAGTCACCTGCTGTTA (SEQ ID NO: 19) | TGCTGCTGGTGATTCTTC (SEQ ID NO: 20) | NM_002982 |
| hVACM-1 | TTGCTCAGATTGGTGACTCCGTCT (SEQ ID NO: 21) | TTCGTCACCTTCCCATTCAGTGGA (SEQ ID NO: 22) | NM_001078 |
| hICAM-1 | ATAACCGCCAGCGGAAGATCAAGA (SEQ ID NO: 23) | CGTGGCTTGTGTGTTCGGTTTCAT (SEQ ID NO: 24) | NM_000201 |
| mTNFα | ACTGAACTTCGGGGTGATCGGTCC (SEQ ID NO: 25) | GTGGGTGAGGAGCACGTAGTCG (SEQ ID NO: 26) | NM_013693 |
| mIL-1β | AACCTGCTGGTGTGTGACGTTC (SEQ ID NO: 27) | CAGCACGAGGCTTTTTGTTGT (SEQ ID NO: 28) | NM_008361 |
| mMIP-2 | CCTGCCAAGGGTTGACTTCA (SEQ ID NO: 29) | TTCTGTCTGGGCGCAGTG (SEQ ID NO: 30) | NM_009140 |

Each of the above-identified Genbank Accessions is hereby incorporated by reference in its entirety.

Dual Luciferase Reporter Assay:

To determine the NF-κB promoter activity in response to TNFα, cells were seeded in 6-well plates (1.5×10⁵ cells/well) overnight and transiently transfected with NF-κB promoter-luciferase constructs or a control luciferase construct pRL-TK (Promega, CA, USA) using either FuGENE6 Transfection Reagent (Roche, Mannheim, Germany) or TransIT-LTI transfection reagent (Mirus Bio) as described previously (Aizawa et al., "Role of Phosphodiesterase 3 in NO/cGMP-mediated Anti-inflammatory Effects in Vascular Smooth Muscle Cells," Circ Res 93:406-13 (2003), which is hereby incorporated by reference in its entirety). pFC-MEKK1 were from Stratagene. Transfected cells were serum-starved for 48 h followed by exposure to TNFα for 6 h. Firefly and Renilla luciferase activities in cell extracts were measured using Dual-Luciferase Reporter Assay System (Promega, CA, USA). The relative luciferase activity was then calculated by normalizing NF-κB promoter-driven firefly luciferase activity to control *Renilla* luciferase activity. Data from all experiments are presented as the relative luciferaseactivity (mean±S.D.) from at least three independent sets of experiments, each with triplicate measurements.

Immunoprecipitation and In Vitro IKK Kinase Assay:

Cell lysates were prepared as described above. 1 mg of cell lysates were incubated with 1-2 µg of anti-IKKα (Santa Cruz, Calif., USA) for 1-2 h, followed by 50µl of 50% of slurry protein A/G plus-Agarose for another 1 h or overnight at 4° C. Immunoprecipitants were then washed two times with lysis buffer and once with kinase buffer without ATP. In vitro kinase assay were performed in kinase buffer containing 20 mM HEPES (pH 7.7), 2 mM $MgCl_2$, 2 mM $MnCl_2$, 10 µM ATP, 5 µCi of $[\gamma-^{32}P]ATP$ (Amersham Biosciences, NJ, USA), 10 mM glycerophosphate, 10 mM NaF, 100 µM $Na_3VO_4$, 1 mM benzamidine, 2 µM PMSF, 1 mM DTT and protease inhibitor cocktail (Sigma, MO, USA) at 30° C. for 30-60 min, in the presence of substrate GST-IκBα (AA 1-54) (kindly provided by Dae-Myung Jue, Catholic University of Korea). Proteins were separated by 12% SDS-PAGE and subjected to autoradiography. Phosphorylation of GST-IκBα was quantified in NIH Image 1.60.

Monocyte Adhesion and Chemotaxis Assay:

For monocyte adhesion assay, HUVECs were plated on 2% gelatin-coated 6-well plates and cultured to confluence. The cells were incubated in 50 µM vinpocetine for 30 min and then were treated with 10 ng/ml TNFα for 6 hours. Human U937 cells were washed 3 times with serum-free RPMI 1640 medium. Approximately 1 ml of the cells (20,000 cells/ml) were put into the wells and incubated for 20 minutes. Then un-adhered cells in the wells were washed out 3 times with serum-free RPMI 1640 medium. The adherent cells were counted in 5 randomly selected optical fields in each well, as previously described (Che et al., "Insulin-like Growth Factor-1 Enhances Inflammatory Responses in Endothelial Cells: Role of Gab1 and MEKK3 in TNF-α-induced c-Jun and NF-κB Activation and Adhesion Molecule Expression," *Circ Res* 90: 1222-30 (2002), which is hereby incorporated by reference in its entirety). Phase-contrast microphotographs of the cells in plates were taken under a microscope (Olympus).

For monocyte chemotaxis assay, rat aortic VSMCs were grown in normal culture medium in 12-well dish until reaching 70-80% confluence, followed by grown in serum-free medium for at least 16 hours. VSMCs were then pretreated with various doses of vinpocetine or vehicle for 30 minutes, and stimulated with TNFα (10 ng/ml) for 9 hours. The conditional medium from each well was collected for further chemotaxis assays. Monocyte chemotaxis was performed by transwell migration using a 24-well Boyden chamber (Corning Life Science, NY, USA) containing a polycarbonate filter with 5-µm pore size. 600 µl of each VSMC-conditional medium was added into duplicate wells in the lower chambers. A 100 µl aliquot of monocytes (THP-1) ($10^6$ cells/100 µl/well) were loaded into each well of the upper chamber. After 90-minute incubation, migrated THP-1 cells on the low surface of each well were collected through centrifugation, and subjected to direct cell counting under microscope. Experiments were performed in triplicate.

Mouse Model of Lung Inflammation:

C57BL/6 mice were purchased from NCI, and 7 to 8 weeks-old mice were used in this study as previously described (Ishinaga et al., "TGF-β Induces p65 Acetylation to Enhance Bacteria-induced NF-κB Activation," *EMBO J* 26:1150-62 (2007), which is hereby incorporated by reference in its entirety). Under the anesthesia, mice were intratracheally inoculated with lipopolysaccharide (LPS, *Escherichia coli* serotype 055:B5, 2 µg per mouse, Sigma) in 50 µl of PBS vehicle or TNFα (500 ng per mouse), or same volume of saline as control for 6 hours. Vinpocetine (10 mg/kg body weight) or equal volume of vehicle control was administered via an intraperitoneal route 2 hours prior to the intratracheal inoculation of LPS or TNFα. Lung tissues were collected and then stored at −80° C. for mRNA expression analysis. For polymorphonuclear neutrophil (PMN) recruitment analysis, broncho-alveolar lavage (BAL) was performed by cannulating the trachea with sterilized PBS, and cells from BAL was stained with Hemacolor (EM Science) after cytocentrifugation (Shandon Cytospin4, Thermo Electronic Co.). Three mice were used for each inoculation group. All animal experiments were approved by the institutional Animal Care and Use Committee at University of Rochester.

Statistical Analysis:

Data were shown as mean±S.D. Statistical evaluation was performed with the StatView 4.0 package (ABACUS Concepts, Berkeley, Calif.). $p<0.05$ was taken as a significant difference.

Example 1: Vinpocetine Inhibits NF-κB Activation in a Variety of Cell Types

Figure 1B:
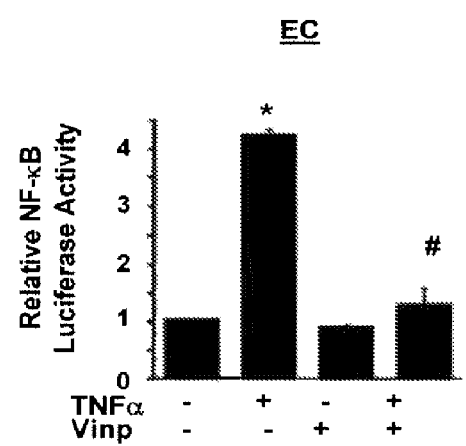
Figure 1C:
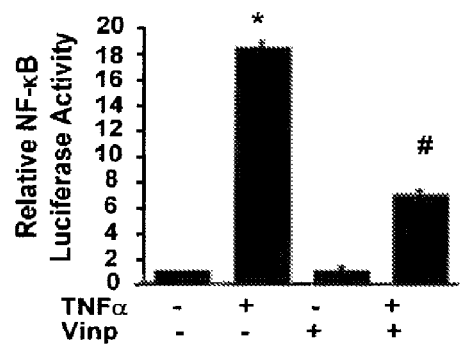
Figure 1D:
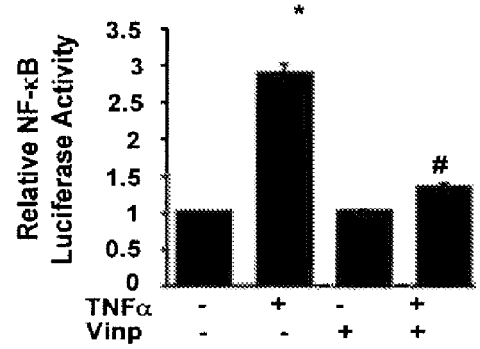

Because NF-κB plays a critical role in regulating inflammatory response, whether vinpocetine acts as an anti-inflammatory agent by inhibiting NF-κB was investigated. The effect of vinpocetine on NF-κB-dependent promoter activity was first evaluated by using luciferase reporter plasmids in a variety of cell types. As shown in FIG. 1A, vinpocetine potently inhibited TNFα-induced NF-κB-dependent promoter activity in vascular smooth muscle cells (VSMCs) in a dose-dependent manner. Similar results were also observed in human umbilical vein endothelial cells (HUVECs, FIG. 1B), human lung epithelial A549 cells (FIG. 1C), and macrophage cell line (RAW264.7) (FIG. 1D). Similarly to TNFα, IL-1- and LPS-induced NF-κB-dependent promoter activity was also inhibited by vinpocetine. It should be noted that no significant cytotoxic effects on cell morphology and viability were observed at the tested doses.

Figure 2:
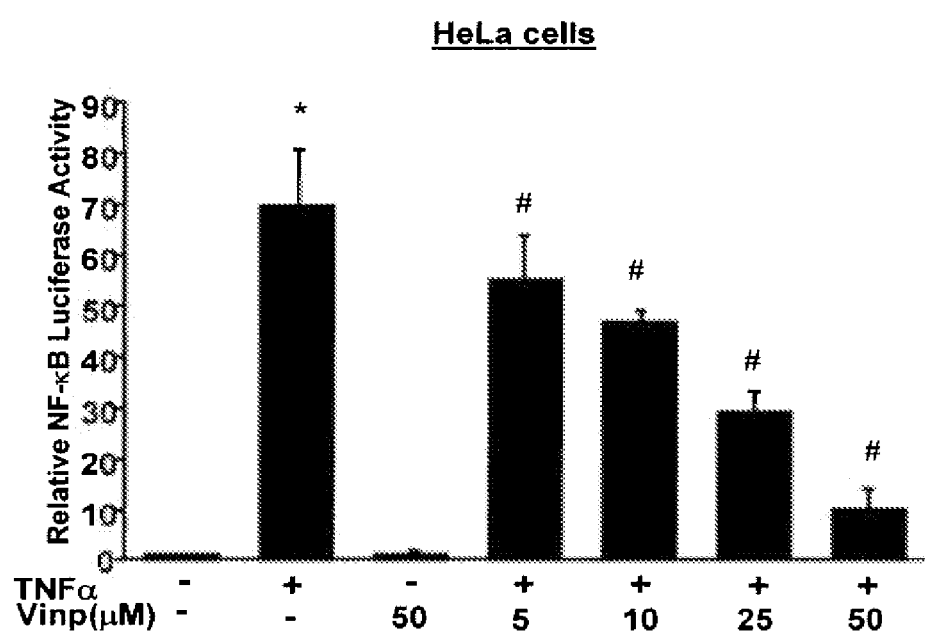
FIG. 2 shows that vinpocetine inhibits TNFα-induced NF-κB-dependent promoter activity in Hela cells. The Hela cells were transfected with the NF-κB-Luc reporter plasmid and stimulated with or without TNFα as described for FIGS. 1A-D, using various doses of vinpocetine injection solution (Vinp), an injectable commercial vinpocetine pharmaceutical composition. Cells were then lysed for luciferase assay. Data represent means±SD of at least three independent experiments and each experiment was performed in triplicate. *P<0.05 vs. control and #P<0.05 vs. TNFα alone.

This experiment was repeated using HeLa cells using substantially the same procedures, except with varying doses of a commercial (injectable) vinpocetine pharmaceutical composition. The observed results show a dose-dependent inhibition of TNFα-induced NF-κB-dependent promoter activity (FIG. 2) that is consistent with the results presented in FIGS. 1A-D.

Figure 3A:
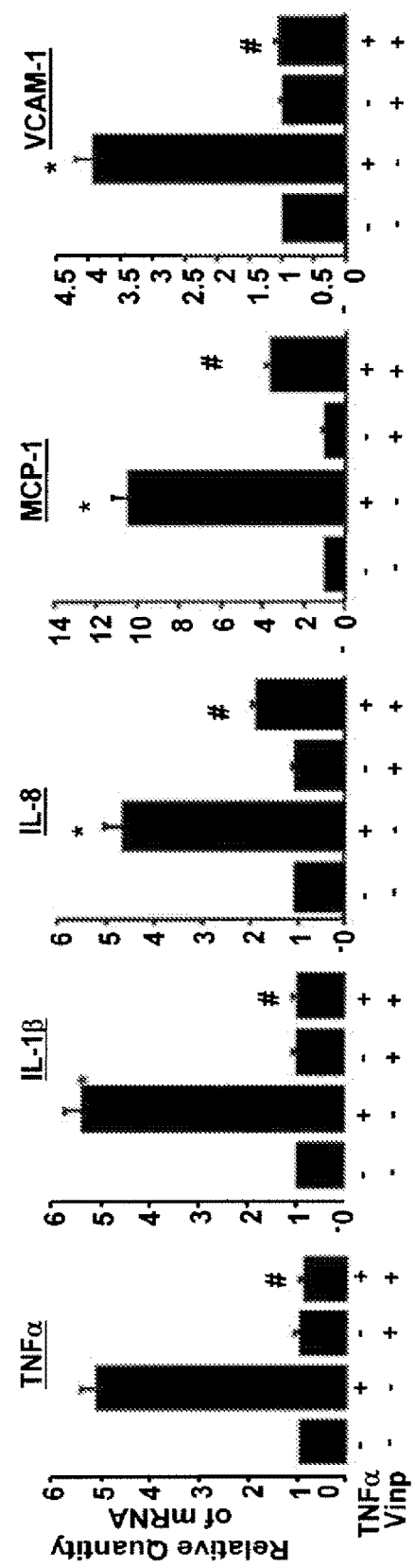
FIGS. 3A-D show that vinpocetine inhibits TNFα-induced expression of pro-inflammatory mediators in a variety of cell types. Rat aortic VSMCs (FIG. 3A), Vascular ECs (HUVECs) (FIG. 3B), Lung Epithelial A549 cells (FIG. 3C) or Macrophage RAW264.7 (FIG. 3D) were treated with or without TNFα (10 ng/ml) for 6 hours in the presence or absence of vinpocetine (50 μM). Expression of TNFα, IL-1β, IL-8, MCP-1 and VCAM-1, ICAM-1, MIP-1 at mRNA levels were measured by Real-time quantitative RT-PCR (Q-PCR). Data represent means±SD of at least three independent experiments and each experiment was performed in triplicate. *p<0.05 vs. control and #p<0.05 vs. TNFα alone.
Figure 3B:
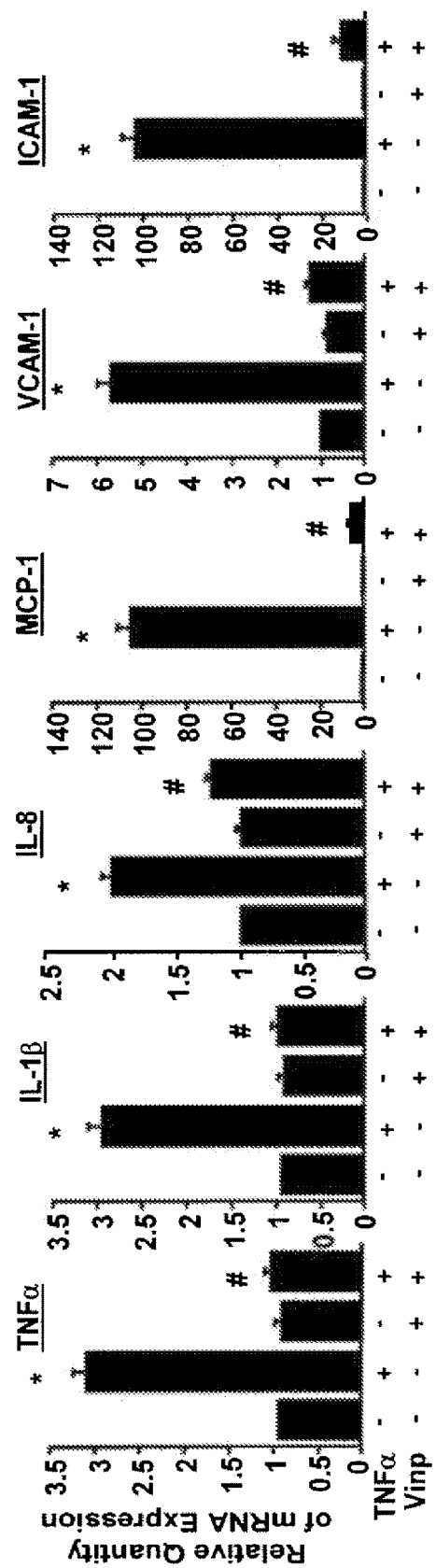
Figure 3C:
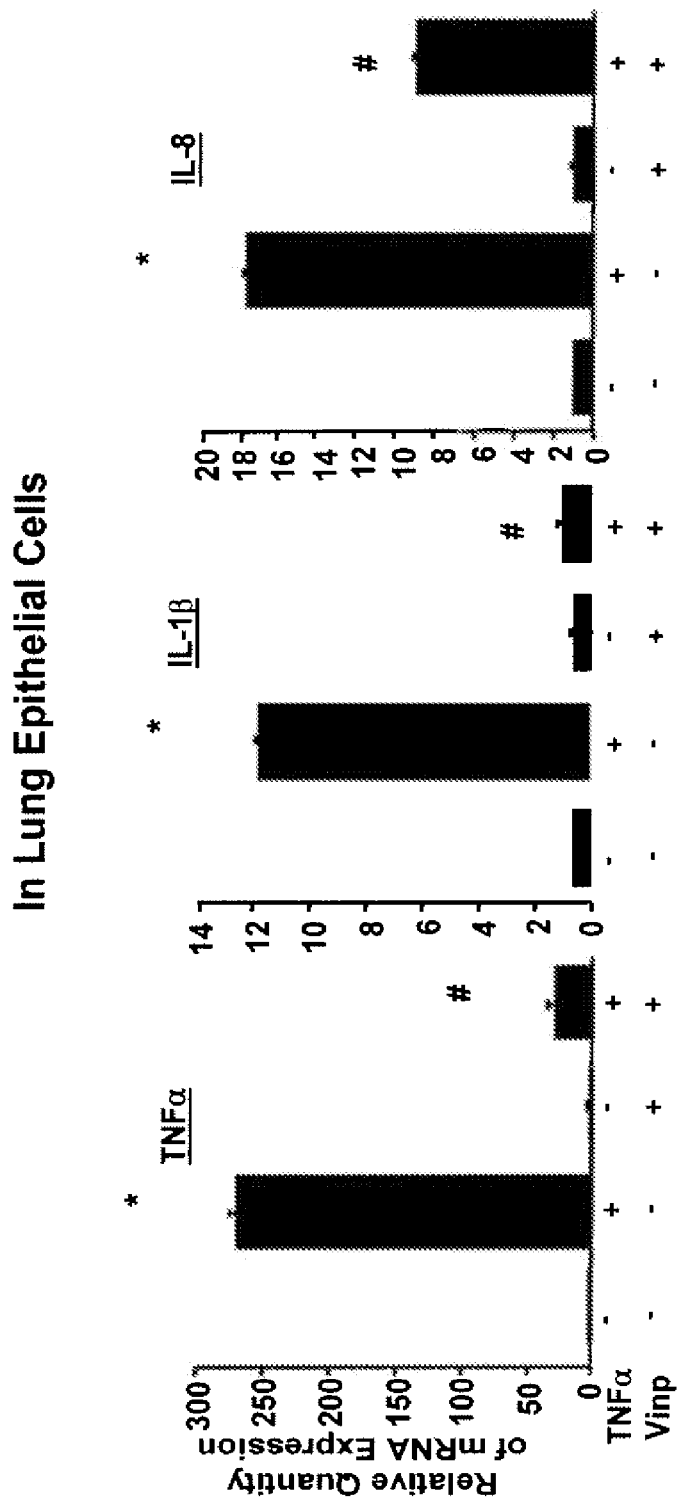
Figure 3D:
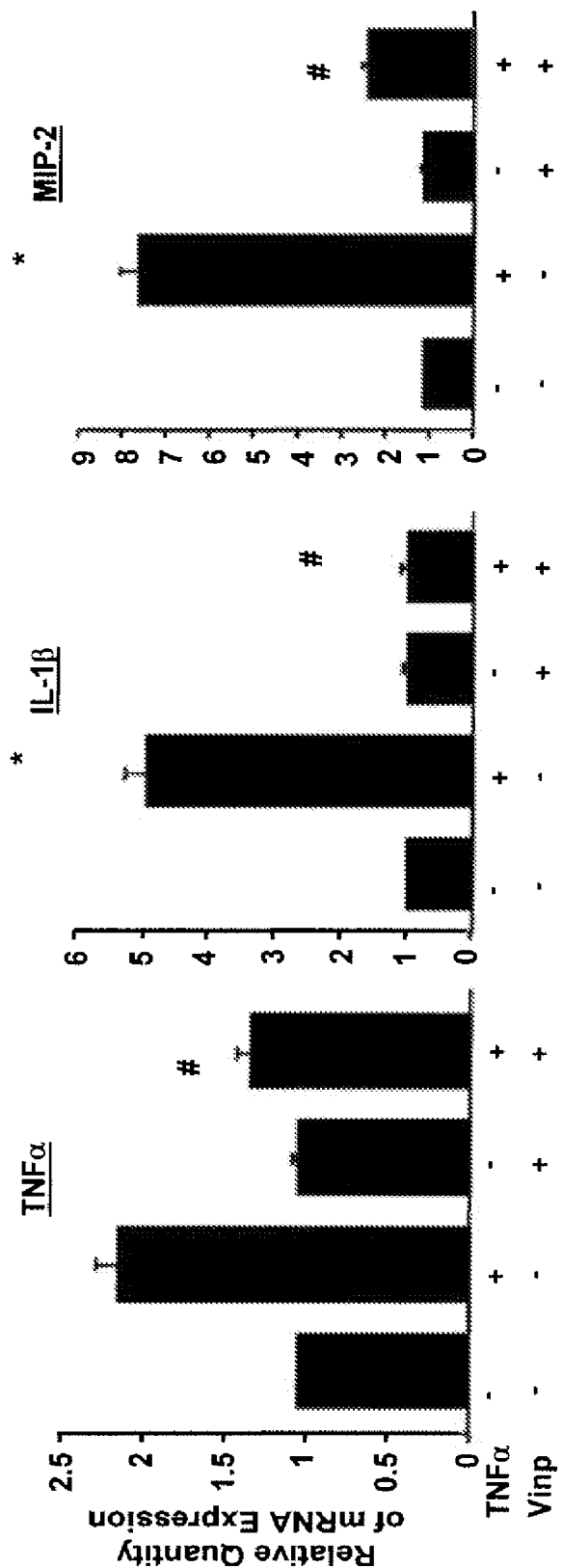

Example 2: Vinpocetine Inhibits TNFα-Induced Pro-Inflammatory Mediators in a Variety of Cell Types Next it was determined whether vinpocetine also inhibits TNFα-induced up-regulation of NF-κB-dependent pro-inflammatory mediators including cytokines, chemokines and adhesion molecules at the mRNA level. As shown in FIG. 3A, vinpocetine potently inhibited TNFα-induced expression of TNFα, IL-1β, I-8, monocot chemotactic protein 1 (MCP-1) and vascular cell adhesion molecule 1 (VCAM-1) in VSMCs, as assessed by real-time RT-PCR analysis. Similarly, vinpocetine was also found to inhibit TNFα-induced expression of TNFα, IL-1β, IL-8, MCP-1, VCAM-1, and intercellular adhesion molecule 1 (ICAM-1) in HUVECs (FIG. 3B), expression of TNFα, IL-1β, and IL-8 in A549 cells (FIG. 3C), and expression of TNFα, IL-1β, and macrophage-inflammatory protein 2 (MIP-2) in RAW264.7 (FIG. 3D).

Figure 4:
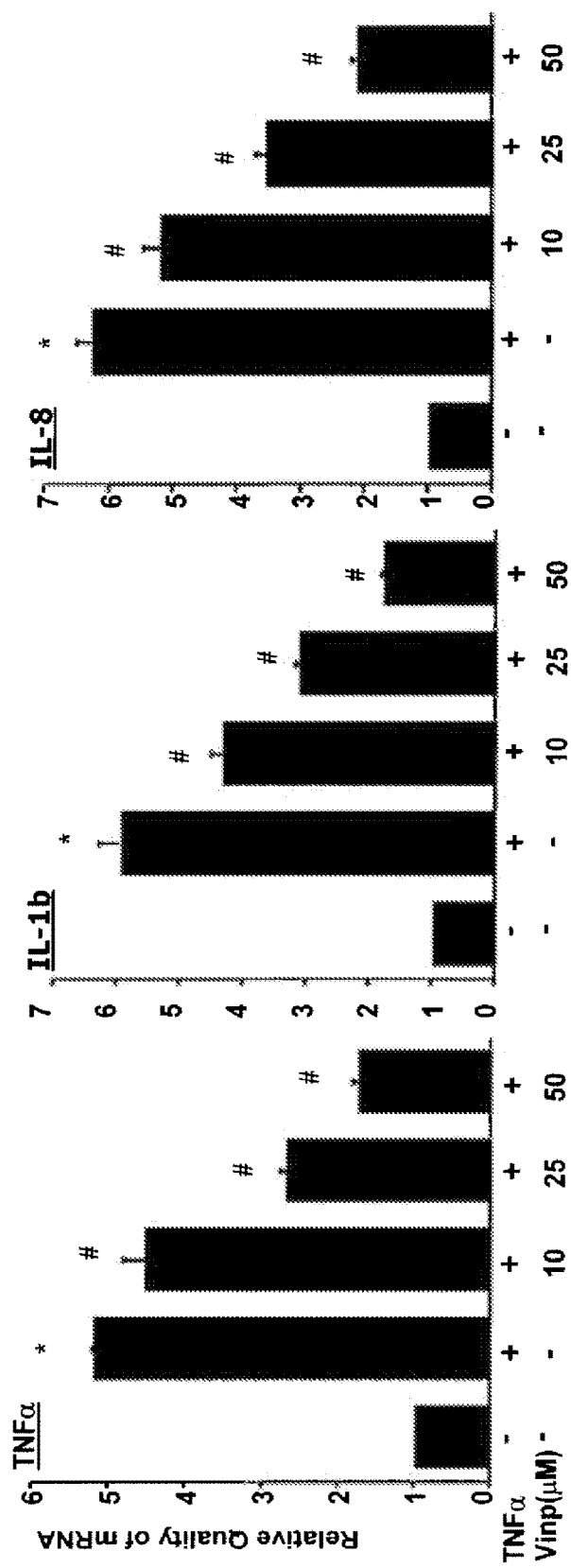
FIG. 4 shows that vinpocetine inhibits TNFα-induced expression of pro-inflammatory mediators dose-dependently in A549 cells. The A549 cells were treated with or without TNFα (10 ng/ml) for 6 hours in the presence or absence of various doses of vinpocetine (Vinp) injection solution (commercial vinpocetine pharmaceutical composition) as indicated. Expression of TNFα, IL-1β, and IL-8 at mRNA levels were measured by Q-PCR. Data represent means±SD of at least three independent experiments and each experiment was performed in triplicate. *p<0.05 vs. control and #p<0.05 vs. TNFα alone.

This experiment was repeated with A549 cells using substantially the same procedures, except with varying doses of a commercial (injectable) vinpocetine pharmaceutical composition. The observed results show a dose-dependent inhibition of TNFα-induced expression of TNFα, IL-1β, and IL-8 (FIG. 4) that is consistent with the results presented in FIGS. 3A-D.

Figure 5A:
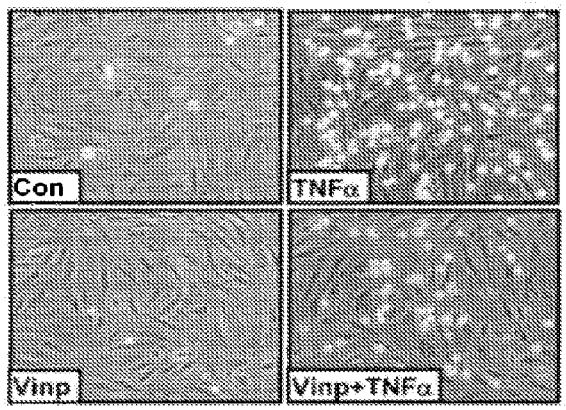
FIGS. 5A-C show that vinpocetine inhibits monocyte adhesion of EC and chemotactic activity of VSMC.
Figure 5B:
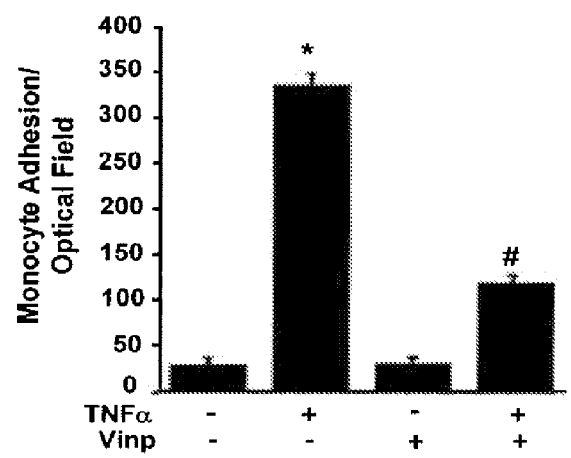
Figure 5C:
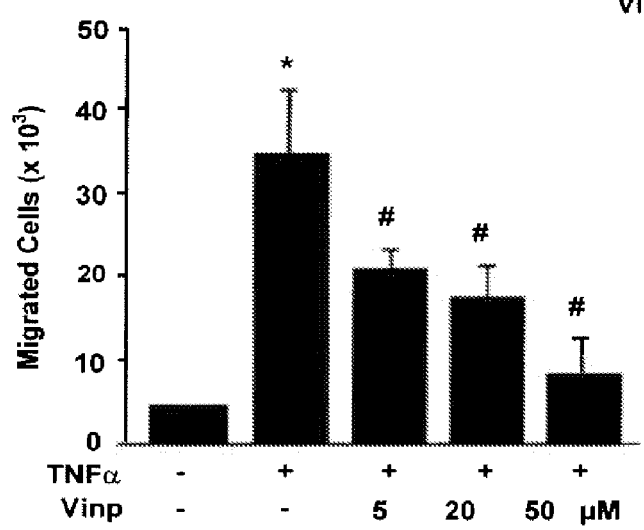

Example 3: Vinpocetine Inhibits Monocyte Adhesion of EC and Chemotactic Activity of VSMC To further evaluate the physiological consequences of the inhibitory effect of vinpocetine on induction of pro-inflammatory mediators, monocyte adhesion and chemotactic activities in ECs and VSMCs were measured, respectively. These cells types are known to be dependent on adhesion molecules (such as ICAM-1 and VCAM-1) and chemokines (such as MCP-1) (Kunsch et al., "Oxidative Stress as a Regulator of Gene Expression in the Vasculature," *Circ Res* 85:753-66 (1999), which is hereby incorporated by reference in its entirety). As shown in FIG. 5A-B, monocyte adhesion to HUVECs was markedly inhibited by vinpocetine, as assessed by adhesion assay. Moreover, vinpocetine also inhibited monocyte chemotaxis to VSMCs induced by TNFα in a dose-dependent manner (FIG. 5C), as measured by transwell migration with Boyden chamber.

Example 4: Vinpocetine Inhibits Lung Inflammatory Response In Vivo

Figure 6A:
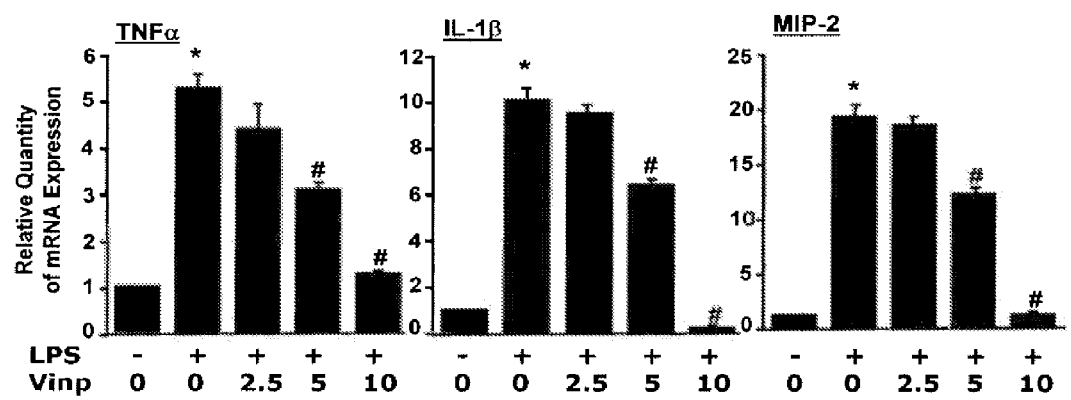
FIGS. 6A-B shows that vinpocetine inhibits lung inflammatory response in vivo.
Figure 6B:
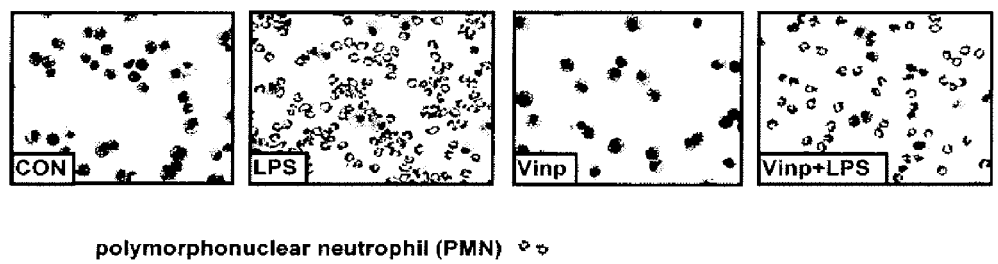

To further confirm whether vinpocetine inhibits inflammatory response in vivo, the effects of vinpocetine on lung inflammation induced by LPS (a well-known potent inducer for lung inflammation) were evaluated using a well-established mouse model (Ishinaga et al., "TGF-β Induces p65 Acetylation to Enhance Bacteria-induced NF-κB Activation," *EMBO J* 26:1150-62 (2007), which is hereby incorporated by reference in its entirety). As shown in FIG. 6A, intraperitoneal (i.p) administration of vinpocetine dose-dependently inhibited induction of TNFα, IL-1β and MIP-2 mRNA expression in the lungs of mice by intratracheal (i.t) administration of LPS. Consistent with these results, vinpocetine also significantly inhibited polymorphonuclear neutrophil (PMN) infiltration in broncho-alveolar lavage (BAL) fluids from the lungs of mice treated with LPS (FIG. 6B). Similarly, vinpocetine also inhibited induction of these inflammatory mediators and PMN infiltration in the lungs of mice by intratracheal (i.t) administration of TNFα. Taken together, it is evident that vinpocetine is a potent inhibitor for NF-κB-activation and the resultant inflammatory response in vitro and in vivo.

Figure 7A:
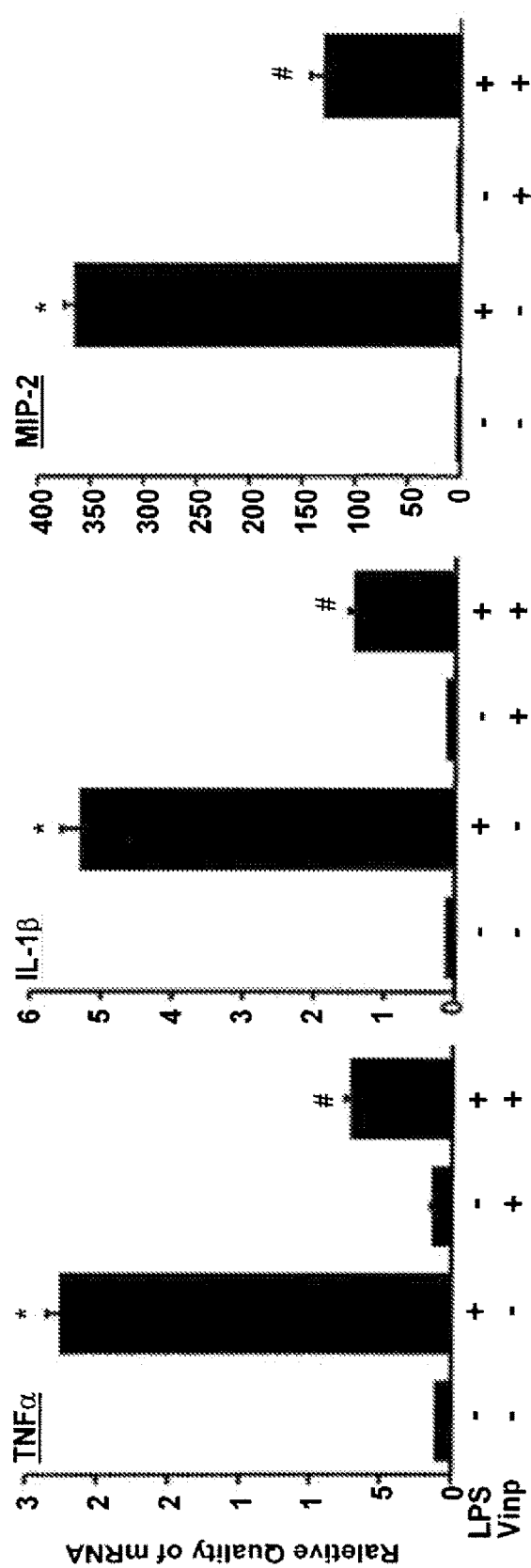
FIG. 7A-C illustrate that vinpocetine inhibits lung inflammatory response in vivo using injectable Vinpocetine solution.
Figure 7B:
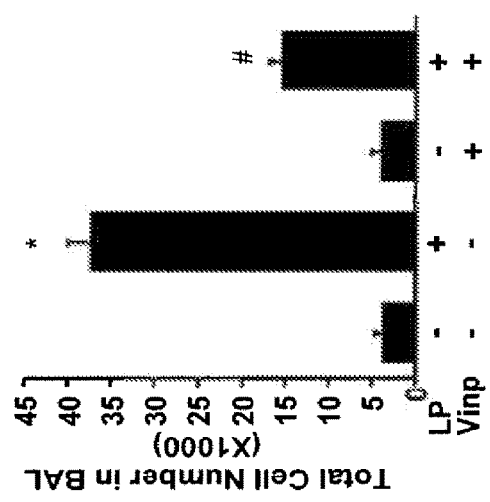
Figure 7C:
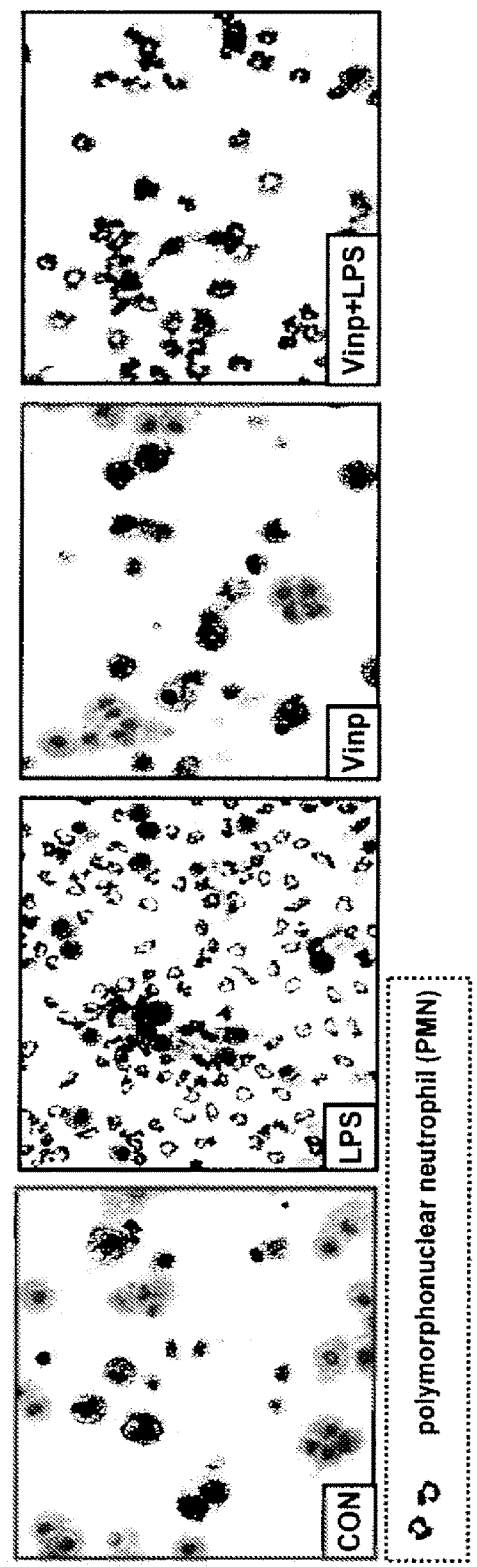

Using this same mouse model, it was also demonstrated that injection of a commercial vinpocetine pharmaceutical composition potently inhibited LPS-induced up-regulation of pro-inflammatory mediators including TNFα, IL-1β, and MIP-2 (FIG. 7A) as well as interstitial infiltration of polymorphonuclear leukocyte (PMN) in the lungs (FIG. 7B-C) by using a mouse lung inflammation model. These results were consistent with the results presented in FIGS. 6A-B.

Example 5: Vinpocetine Inhibits TNFα-Induced NF-κB Activation by Targeting IKK

Figure 8A:
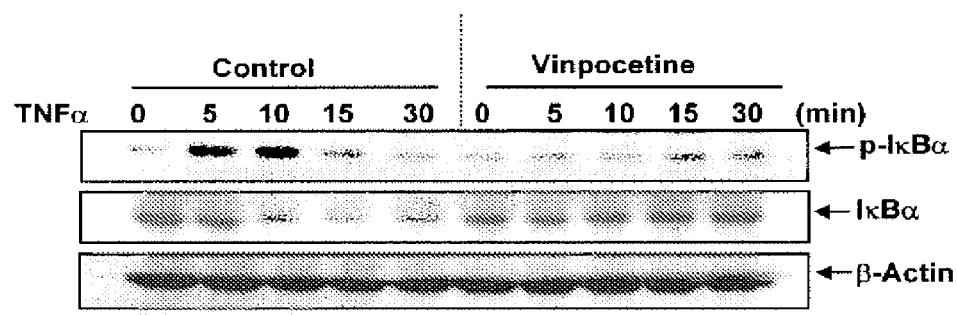
FIGS. 8A-H shows that vinpocetine inhibits TNFα-induced NF-κB activation by targeting IKK.

Having identified vinpocetine as a novel inhibitor for NF-κB-dependent inflammation, the molecular target of vinpocetine was then identified. Because IKK-dependent phosphorylation and degradation of IκBα plays a very important role in mediating TNFα-induced activation of NF-κB and the subsequent up-regulation of NF-κB-dependent pro-inflammatory mediators, the effects of vinpocetine on IκB phosphorylation and IκBα degradation induced by TNFα in VSMCs was evaluated by Western blot analysis using anti-phospho-Ser32 of IκBα antibody and total IκB antibody, respectively. As shown in FIG. 8A, TNFα induced phosphorylation and degradation of IκBα in a time-dependent manner and pretreatment with vinpocetine markedly inhibited TNFα-induced IκBα phosphorylation and degradation. Similar results were also observed in other cell types, including ECs and macrophage. These results thus suggest that vinpocetine inhibits TNFα-induced NF-κB activation through inhibition of IκBα phosphorylation and degradation.

Figure 8B:
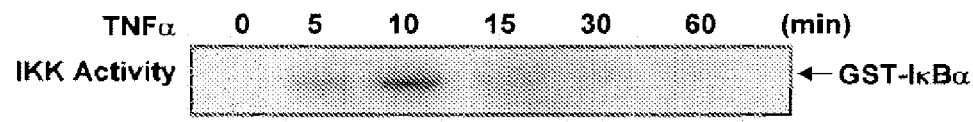

Because IKK is known as the major upstream kinase for IκBα phosphorylation and degradation, whether vinpocetine inhibits IκB phosphorylation and degradation via inhibition of IKK was determined. TNFα-induced activation of IKK was confirmed by performing IKK kinase assay in TNFα-stimulated VSMCs. The crude cell lysates from treated VSMCs were first immunoprecipitated with an anti-IKKα antibody and IKK kinase activity was then measured in vitro with IKK immune complexes incubated with the substrate GST-IκBα in the presence of $[\gamma{-}^{32}P]$-ATP. As shown in FIG. 8B, IKK activity was undetectable in non-stimulated cells, became evident at 5 min upon TNFα treatment, peaked at 10 min, and declined thereafter. Interestingly, vinpocetine inhibited TNFα-induced IKK activity in a dose-dependent manner (FIGS. 8C and 8D), thereby suggesting that vinpocetine inhibits TNFα-induced NF-κB-activation at the level of or upstream of IKK but not at the level of IκBα.

Figure 8C:
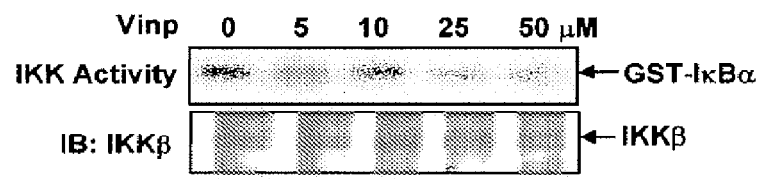
Figure 8D:
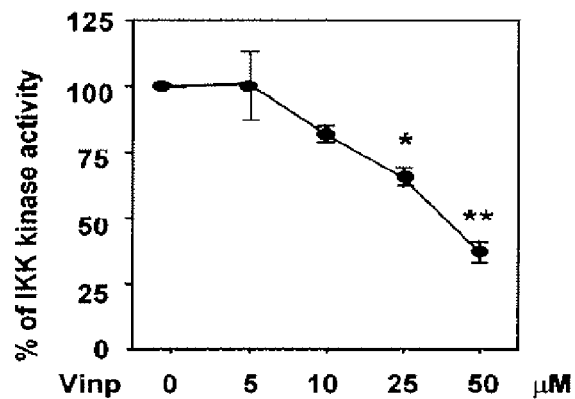
Figure 8E:
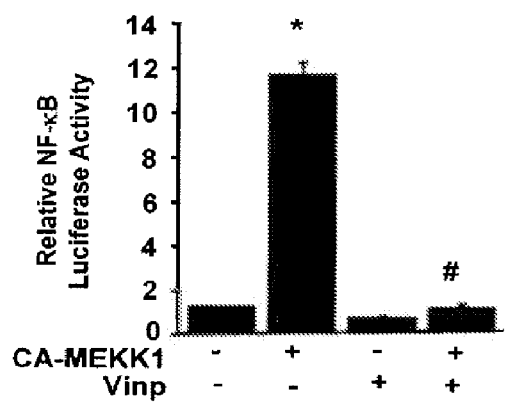
Figure 8F:
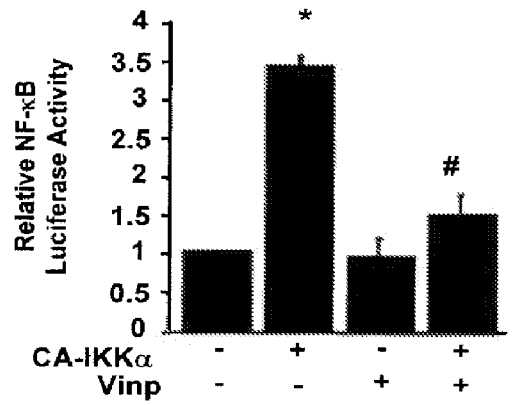
Figure 8G:
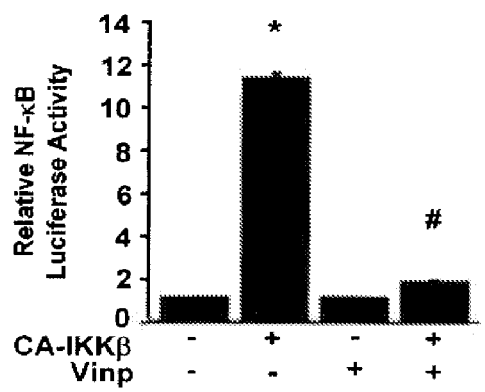
Figure 8H:
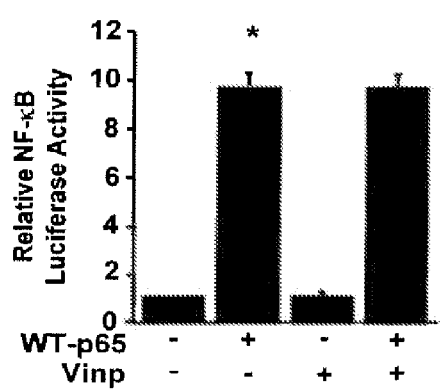

Next it was determined whether vinpocetine inhibits TNFα-induced NF-κB activation via inhibition of IKK or its major upstream kinase MEKK1 (Nemoto et al., "Coordinate Regulation of IκB kinases by mitogen-activated protein kinase 1 and NF-κB-inducing kinase," *Mol Cell Biol.* 18:7336-43 (1998), which is hereby incorporated by reference in its entirety). As shown in FIG. 8E, overexpression of constitutively active MEKK1 (CA-MEKK1) alone induced potent NF-κB-dependent luciferase activity. Pretreatment with vinpocetine significantly inhibited CA-MEKK1-induced NF-κB activation, indicating that vinpocetine acts at the level or downstream of MEKK1. Furthermore, vinpocetine inhibited NF-κB activation induced by expressing constitutively active IKKαCA-IKKα and IKKβCA-IKKβ (FIGS. 8F and 8G) but not by expressing wild type (WT) NF-κB p65 subunit (FIG. 8H). Collectively, these data indicate that vinpocetine inhibits TNFα-induced NF-κB activation by targeting IKK.

Example 6: Vinpocetine Inhibits IKK Kinase Activity Via an Indirect Mechanism

Figure 9A:
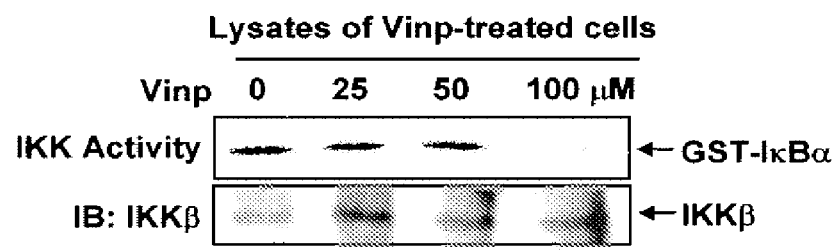
FIGS. 9A-B shows the effects of vinpocetine on inhibition of IKK activity. IKK kinase activity was analyzed by in an immune complex kinase assay. IKK immune complex was obtained by immunoprecipitation from VSMCs treated with TNFα for 10 minutes. Kinase assays were conducted with GST-IκBα and [γ-$^{32}$P]ATP in the presence of cell lysates prepared from VSMCs preincubated with vinpocetine at various concentrations as indicated.
Figure 9B:
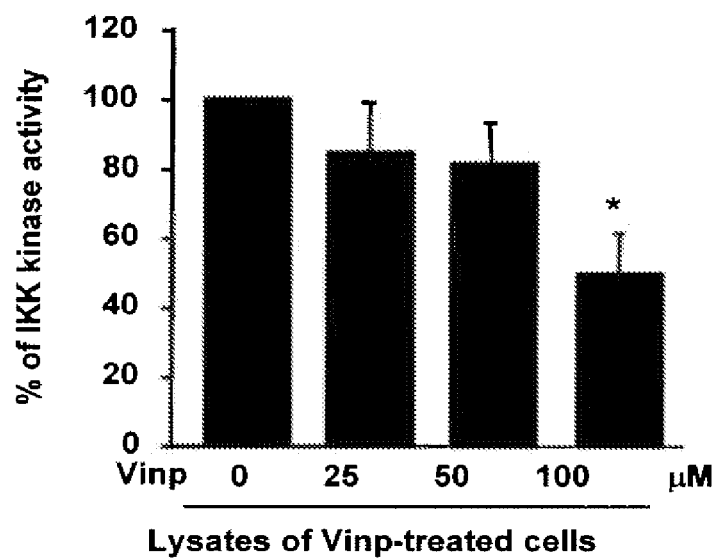

To determine whether vinpocetine directly targets on IKK, the effects of vinpocetine on inhibition of IKK kinase activity were examined by directly applying vinpocetine to the IKK immune complex in the test tube. No significant inhibitory effect of vinpocetine on IKK activity was observed when vinpocetine was directly applied to IKK. Failure of vinpocetine to directly inhibit IKK activity might be due to that vinpocetine needs to be biotransformed in the cell to another active intermediate product that is capable of inhibiting IKK activity. To explore this possibility, the effects of cell lysates prepared from vinpocetine-treated VSMCs on inhibition of IKK kinase activity were assessed. As shown in FIG. 9A-B, cell lysates prepared from cells treated with vinpocetine inhibited IKK activity, suggesting that a biotransformed product from vinpocetine (or vinpocetine metabolite) may be responsible for the inhibition of IKK activity. Cell lysates from 100 μM vinpocetine treatment was required to achieve a significant effect on IKK inhibition ex vivo (FIG. 9B). However, much lower concentrations of vinpocetine were required to block IKK activation in intact cells (FIG. 8C-D). This discrepancy is most likely due to the dilution (about 5-10 fold) of cellular contents in the cell lysate compared with those inside the cell.

Figure 10:
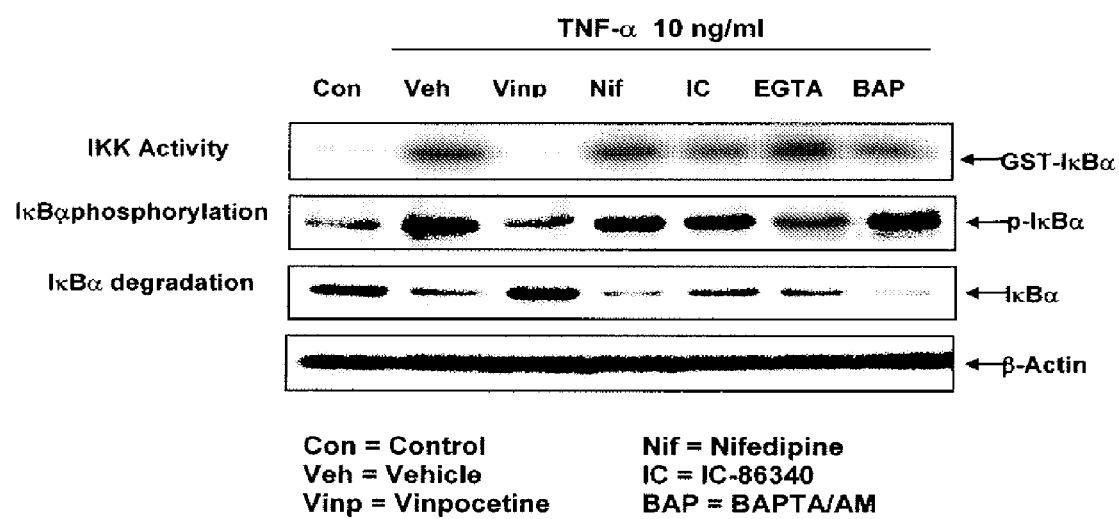
FIG. 10 shows the effects of $Ca^{2+}$ and PDE inhibitor on TNFα-induced IKK kinase activity, IκB phosphorylation, and IκB degradation. Rat aortic VSMCs were treated with TNFα (10 ng/ml) for 10 minutes in the presence of either 50 μM vinpocetine, 30 μM nifedipine ($Ca^{2+}$ channel blocker), 15 μM IC86340 (PDE1 inhibitor), 2 mM EGTA (extracellular $Ca^{2+}$ chelator), or 30 μM BAPTA/AM (intracellular $Ca^{2+}$ chelator). Representative autoradiogram shows IKK kinase activity analyzed by an IKK immune complex kinase assay as described. Western Blotting analysis was carried out to evaluate the levels of phosphorylated IκBα total IκBα and β-actin. Data represent at least three independent experiments.

Example 7: The Inhibitory Effect of Vinpocetine on IKK Kinase Activity is Independent of its Known Actions on PDE1 Activity and $Ca^{2+}$ Regulation On the basis of previous report showing that increased intracellular cAMP or cGMP inhibits NF-κB-dependent transcriptional activity and expression of inflammatory mediators in VSMCs via a PKA-dependent mechanism (Aizawa et al., "Role of Phosphodiesterase 3 in NO/cGMP-mediated Anti-inflammatory Effects in Vascular Smooth Muscle Cells," *Circ Res* 93:406-13 (2003), which is hereby incorporated by reference in its entirety) and vinpocetine is a well-known PDE1 inhibitor (Bönöezk et al., "Role of Sodium Channel Inhibition in Neuroprotection: Effect of vinpocetine," *Brain Res Bull* 53:245-54 (2000); Hagiwara et al., "Effects of vinpocetine on Cyclic Nucleotide Metabolism in Vascular Smooth Muscle," *Biochem Pharmacol* 33:453-7 (1984), each of which is hereby incorporated by reference in its entirety), it was determined whether the inhibitory effect of vinpocetine on NF-κB signaling is mediated by inhibition of PDE1. The effects of specific PDE1 inhibitors on NF-κB transcriptional activity were examined. It was found that, IC86340, a PDE1 selective inhibitor that inhibited VSMC growth (Nagel et al., "Role of Nuclear $Ca^{2+}$/Calmodulin-stimulated Phosphodiesterase 1A in Vascular Smooth Muscle Cell Growth and Survival," *Circ Res* 98:777-84 (2006), which is hereby incorporated by reference in its entirety), did not exhibit any inhibitory effects on TNFα-induced IκB phosphorylation. Because in addition to PDE1 vinpocetine is also known to inhibit $Ca^{2+}$-channels (Kaneko et al., "The Use of Xenopus Oocytes to Evaluate Drugs Affecting Brain $Ca^{2+}$ Channels: Effects of Bifemelane and Several Nootropic Agents," *Eur J Pharmacol* 189:51-8 (1990); Tretter et al., "The Neuroprotective Drug vinpocetine Prevents Veratridine-induced $[Na^+]_i$ and $[Ca^{2+}]_i$ Rise in Synaptosomes," *Neuroreport* 9:1849-53 (1998), each of which is hereby incorporated by reference in its entirety) in neurons, it was determined whether the inhibitory effect of vinpocetine on TNFα-induced IKK activity may involve $Ca^{2+}$ influx or intracellular $Ca^{2+}$ homeostasis. The effects of nifedipine, a $Ca^{2+}$-channel blocker, EGTA an extracellular $Ca^{2+}$ chelator, or BAPTA/AM, an intracellular $Ca^{2+}$ chelator, on TNFα-induced IKK kinase activity, IκB phosphorylation, and IκB degradation were examined in VSMCs. As shown in FIG. 10, none of them exhibited any significant inhibitory effects on TNFα-induced IKK kinase activity, IκB phosphorylation and IκB degradation. Together, it is proper conclude from these data that vinpocetine inhibits TNFα-induced IKK-dependent NF-κB activation independently of its known actions on PDE1 and $Ca^{2+}$ regulation, thereby revealing a novel action of vinpocetine on IKK-NF-κsignaling.

Figure 11:
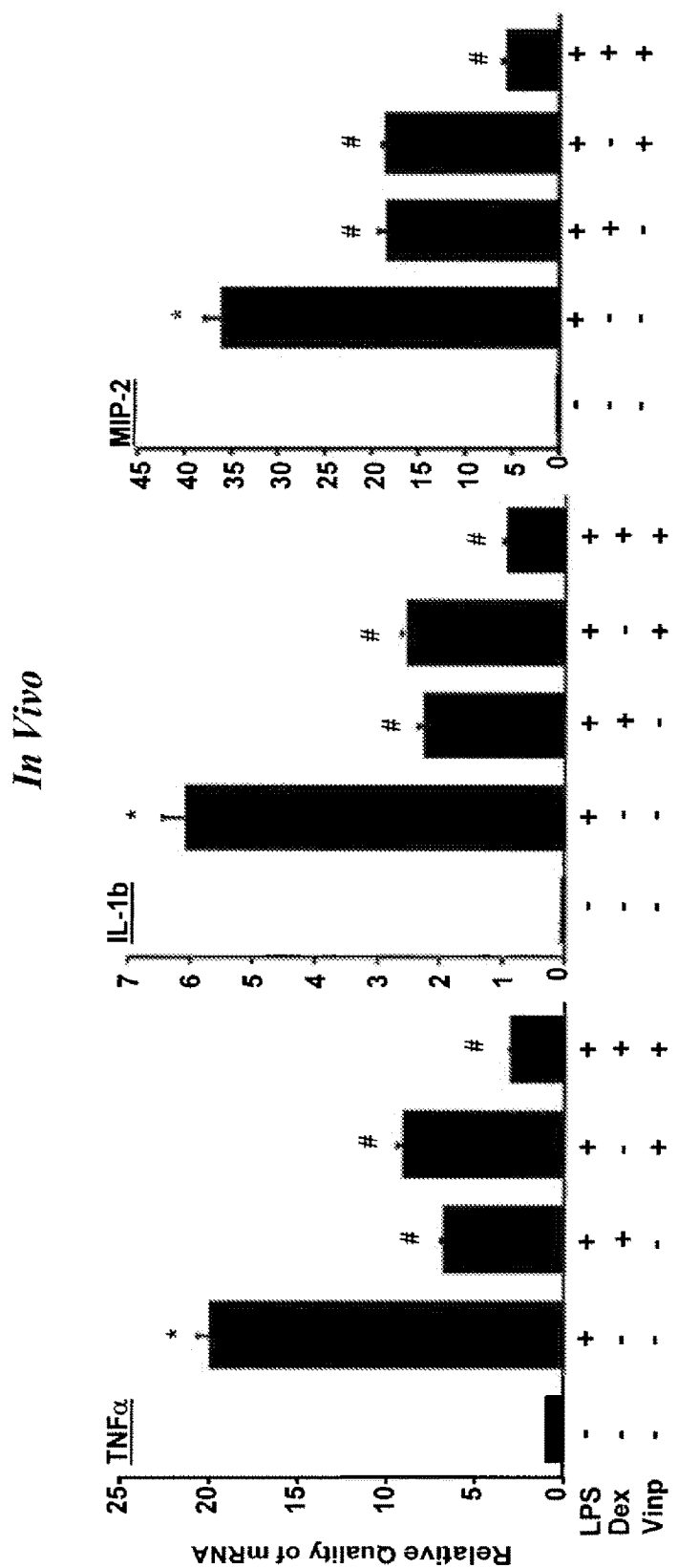
FIG. 11 shows that vinpocetine reduces the dosage of dexamethasone in inhibiting lung inflammatory response in vivo. Intraperitoneal (i.p.) administration of dexamethasone (500 μg/kg body weight) alone or in conjunction with vinpocetine (5 mg/kg body weight) significantly inhibited induction of TNFα, IL-1b and MIP-2 mRNA in the lungs of mice by intratracheal (i.t.) administration of LPS (2 μg/mouse). Data represent means±SD, n=3. *P<0.05 vs. untreated group. #P<0.05 vs. LPS alone.

Example 8: Vinpocetine & Dexamethasone Combination Therapy for LPS-Induced Inflammation In Vivo FIG. 11 shows that vinpocetine reduces the dosage of dexamethasone in inhibiting lung inflammatory response in vivo. Mice were administered LPS (2 μg/mouse) intratracheally (i.t.), which induces an inflammatory response indicated by induction of TNFα, IL-13 and MIP-2 mRNA (see LPS+/Dex−/Vinp− bars in each graph). Intraperitoneal (i.p.) administration of dexamethasone alone (500 μg/kg body weight) and a commercial vinpocetine pharmaceutical composition alone (5 mg/kg body weight) each inhibited induction of TNFα, IL-1β and MIP-2 mRNA in the lungs of mice. When dexamethasone and vinpocetine were used in combination, the combination significantly inhibited induction of TNFα, IL-1β and MIP-2 mRNA in the lungs of mice at greater levels when compared to either drug alone. These two compounds may use different mechanisms to inhibit inflammation, and therefore the combination therapy may be particularly effective for treating inflammation. It is believed that this combination produces a synergistic effect rather than simply an additive effect.

Discussion of Examples 1-8

Of particular interest in this study is the first identification of vinpocetine as a novel anti-inflammatory agent in vitro and in vivo. Inflammation is a hallmark of a variety of important human diseases including, among others, atherosclerosis (Libby et al., "Inflammation and Atherosclerosis," *Circulation* 105:1135-43 (2002); Libby, "Inflammation in Atherosclerosis," *Nature* 420:868-74 (2002), each of which is hereby incorporated by reference in its entirety), lung inflammatory disease (Tetley, "Inflammatory Cells and Chronic Obstructive Pulmonary Disease," *Curr Drug Targets Inflamm Allergy* 4:607-18 (2005), which is hereby incorporated by reference in its entirety), and arthritis (Okamoto, "NF-κB and Rheumatic Diseases," *Endocr Metab Immune Disord Drug Targets* 6:359-72 (2006), which is hereby incorporated by reference in its entirety). Steroids have long been used in the clinic as the major therapeutic anti-inflammatory agent. Although steroids indeed exhibit a potent anti-inflammatory effect, inappropriate use of steroids cause serious side effects in patients. Thus, developing novel anti-inflammatory agents is currently in high demand. Among various efforts that have been put into drug discovery over the past decades, natural products still remain a highly promising source of new drug candidates due to fewer side effects than comparable pharmaceutical products. Vinpocetine, a derivative of alkaloid vincamine, has long been used in the clinic for the treatment of cerebrovascular disorder and cognitive impairment. Vinpocetine is well known to enhance cerebral circulation and cognitive function and is currently used as a dietary supplement in many countries for preventative treatment of cerebrovascular disorder and related symptoms associated with aging. Large clinical trials with vinpocetine indicate that vinpocetine dilates blood vessels, enhances circulation in the brain, enhances oxygen utilization and glucose uptake from blood and thus activates cerebral metabolism and neuronal ATP bio-energy production. In addition, vinpocetine also elicits neuronal protection effects which increase resistance of the brain to hypoxia and ischemic injury. Vinpocetine was shown to easily cross the blood-brain barrier, which makes vinpocetine one of the rather few drugs that exert a potent, favorable effect on the cerebral circulation. In the examples presented above, vinpocetine was identified as a potent anti-inflammatory agent in vitro and in vivo. This novel finding, together with the facts that vinpocetine is purified from natural products and has been already used in the clinic for decades, makes vinpocetine a highly promising candidate anti-inflammatory agent for the treatment of inflammatory diseases such as atherosclerosis, lung inflammatory disease, and arthritis (among others).

Another interesting finding is that the inhibitory effect of vinpocetine on NF-κB-dependent inflammation is independent of its known actions on PDE1 and $Ca^{2+}$ regulation. The first molecular target identified for vinpocetine was $Ca^{2+}$/calmodulin-stimulated phosphodiesterases (PDEs) (Bönöezk et al., "Role of Sodium Channel Inhibition in Neuroprotection: Effect of Vinpocetine," *Brain Res Bull* 53:245-54 (2000), which is hereby incorporated by reference in its entirety). PDEs, by catalyzing the hydrolysis of cAMP and cGMP, play critical roles in controlling intracellular cyclic nucleotide levels and compartmentation. PDEs constitute a large superfamily of enzymes grouped into eleven broad families based on their distinct kinetic properties, regulatory mechanisms, and sensitivity to selective inhibitors (Yan et al., "Functional Interplay Between Angiotensin II and Nitric Oxide: Cyclic GMP as a Key Mediator," *Arterioscler Thromb Vase Biol* 23:26-36 (2003), which is hereby incorporated by reference in its entirety). Four major families of PDEs have been identified in VSMCs, including $Ca^2$/calmhnodulin-stimulated PDE1, cGMP-inhibited PDE3, cAMP-specific PDE4, and cGMP-specific PDE5. The positive vascular effect in cerebral vasodilation of vinpocetine is at least partially due to its effect on PDE1 inhibition. However, in contrast to the involvement of PDE1 in vinpocetine-elicited cerebral vasodilation, inhibition of NF-κB-dependent inflammation by vinpocetine is evidently independent of PDE1 because IC86340, a specific inhibitor for PDE1 (Nagel et al., "Role of Nuclear $Ca^{2+}$/Calmodulin-stimulated Phosphodiesterase 1A in Vascular Smooth Muscle Cell Growth and Survival," *Circ Res* 98:777-84 (2006), which is hereby incorporated by reference in its entirety), exhibited no significant inhibitory effect on IKK activation, IκB phosphorylation, and degradation (FIG. 10) as well as NF-κB-activation.

In addition to functioning as a PDE1 inhibitor, vinpocetine is also capable of interacting with glutamate receptor as well as inhibiting voltage-gated $Ca^{2+}$-channels in neurons at a relative high concentration, and thus regulating $Ca^{2+}$ signaling (Bönöezk et al., "Role of Sodium Channel Inhibition in Neuroprotection: Effect of Vinpocetine," *Brain Res Bull* 53:245-54 (2000), which is hereby incorporated by reference in its entirety). Moreover, vinpocetine inhibits neuronal voltage-dependent $Na^{2+}$-channels and protects neurons against a $Na^+$ influx (Bönöezk et al., "Role of Sodium Channel Inhibition in Neuroprotection: Effect of Vinpocetine," *Brain Res Bull* 53:245-54 (2000), which is hereby incorporated by reference in its entirety). These effects at least partially contribute to the neuroprotective effect of vinpocetine. In the above examples it was found, however, that decreasing intracellular $Ca^{2+}$ concentration by BAPTA/AM, depleting extracellular $Ca^{2+}$ by EGTA, or inhibiting voltage-gated $Ca^{2+}$-channel by nifedipine, did not significantly affect the ability of vinpocetine on IKK kinase activity, IκB phosphorylation, and IκB degradation (FIG. 10) or NF-κB-dependent transcriptional activity. Moreover, voltage-gated sodium channel antagonist, tetrodotoxin, did not alter the effect of vinpocetine on NF-κB-dependent transcription. Together these data indicate that the anti-inflammatory effect of vinpocetine is independent of its known actions on $Ca^{2+}$ and $Na^+$ channels, revealing a novel action of vinpocetine.

Figure 12:
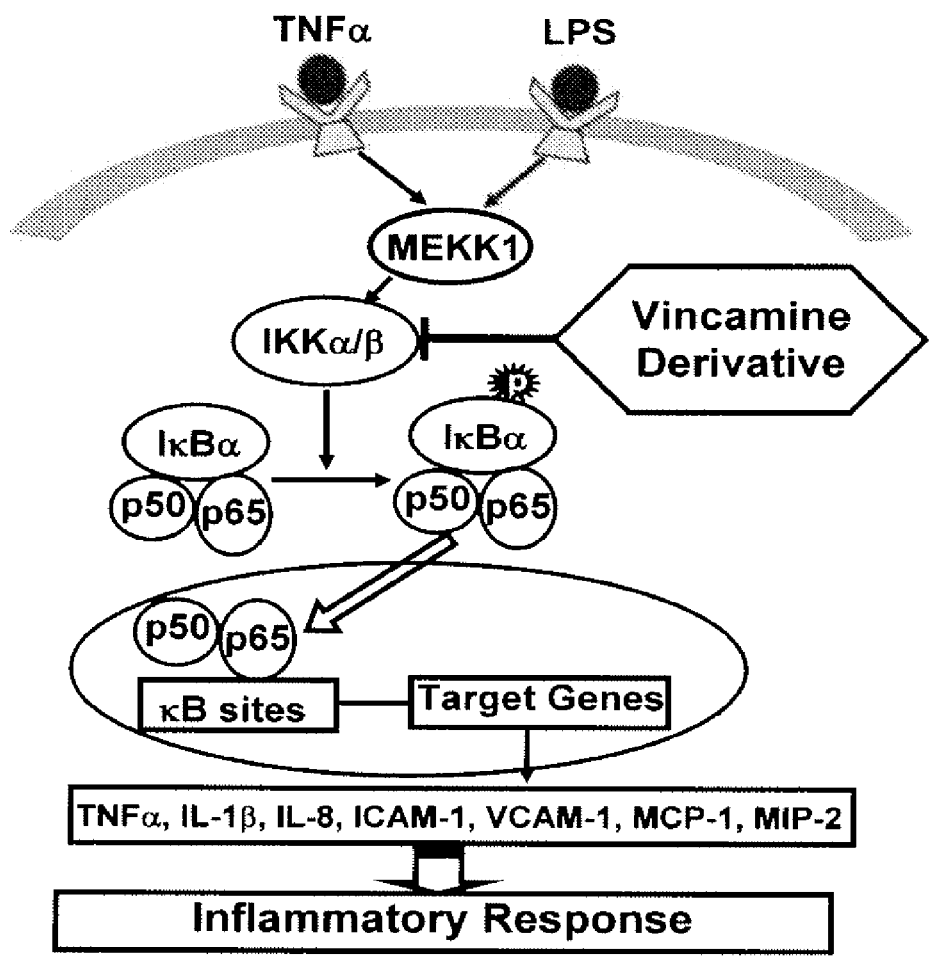
FIG. 12 is a schematic diagram depicting how vinpocetine inhibits NP-κB-dependent inflammatory response in vitro and in vivo. As indicated, vinpocetine inhibits NF-κB-dependent inflammatory response by targeting IKK, independently of its well-known action on PDE1 and $Ca^{2+}$ regulation.

Interestingly, the results suggest that the targeting site of vinpocetine on NF-κB signaling is likely to be IKK (FIG. 12). Vinpocetine, when applied directly to the IKK kinase reaction buffer in the test tube, did not inhibit IKK activity. However, cell lysates from vinpocetine-treated cells inhibited IKK activity by 50% (FIGS. 9A-B). These observations may be explained by the possibility that vinpocetine after its cellular uptake is biotransformed to an intermediate reactive product (a metabolite) that is able to inhibit IKK activity. However, it should be noted that the data do not preclude the involvement of an as yet to be identified signaling intermediate. The exact molecular mechanism by which vinpocetine administration inhibits IKK activity remains to be determined.

The presented data further indicate that a commercially available, injectable vinpocetine formulation, which has been widely used in patients, also has potent anti-inflammatory effect. This commercial formulation was suitable to significantly inhibit TNFα-induced NF-κB activation (FIG. 2) and the subsequent induction of pro-inflammatory mediators (TNFα, IL-1β, and IL-8) (FIG. 4) in a dose dependent manner in vitro. Vinpocetine injection also potently inhibited LPS-induced up-regulation of pro-inflammatory mediators including TNFα, IL-1β, and MIP-2 (FIG. 7A) as well as interstitial infiltration of polymorphonuclear leukocyte (PMN) in the lungs (FIGS. 7A-B) in a mouse lung inflammation model. Finally, when used in a combination therapy with dexamethasone, vinpocetine injection was sufficient to reduce the effective dosage of dexamethosone while inhibiting LPS-induced up-regulation of pro-inflammatory mediators (TNFα, IL-1β, and MIP-2) (FIG. 1) using the same mouse model of lung inflammation.

In conclusion, it is evident that vinpocetine acts as a novel anti-inflammatory agent in vitro and in vivo. Vinpocetine inhibits NF-κB-dependent inflammatory response by targeting IKK, independently of its well-known action on PDE1 and $Ca^{2+}$ regulation, and independent of its known role on $Ca^{2+}$ and $Na^+$ channels. Given that vinpocetine has already been clinically approved to be safe, the present investigation should lead to development of novel therapeutic strategies for the treatment of various mammalian inflammatory diseases.

Based on the successful use of vinpocetine, it is believed that other vincamine derivatives that share similar structure and function are promising for the treatment or prevention of inflammatory diseases in mammalian patients. The use of vinpocetine, alone or in combination with therapeutic agents other than selective COX-2 inhibitors, such as corticosteroids, angiotensin II receptor (type 1) antagonists, angiotensin-converting enzyme (ACE) inhibitors, is particularly preferred. Likewise, the use of vincamine derivatives other than vinpocetine, alone or in combination with other therapeutic agents such as corticosteroids, angiotensin II receptor (type 1) antagonists, ACE inhibitors, and NSAIDs is also preferred.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

All of the features described herein (including any accompanying claims, abstract and drawings), and/or all of the steps of any method or process so disclosed, may be combined with any of the above aspects in any combination, except combinations where at least some of such features and/or steps are mutually exclusive.

What is claimed:

1. A method of treating otitis media, the method comprising administering to a patient in need thereof a therapeutically effective amount of (+)-vinpocetine or a salt thereof and a therapeutically effective amount of a non-steroidal anti-inflammatory drug.

2. The method of claim 1 wherein the non-steroidal anti-inflammatory drug is selected from the group consisting of: ibuprofen (2-(isobutylphenyl)-propionic acid); methotrexate (N-[4-(2,4 diamino 6-pteridinyl-methyl]methylamino]benzoyl)-L-glutamic acid); aspirin (acetylsalicylic acid); salicylic acid; diphenhydramine (2-(diphenylmethoxy)-NN-dimethylethylamine hydrochloride); naproxen (2-naphthaleneacetic acid, 6-methoxy-9-methyl-, sodium salt, (−)); ketorolac (1H-Pyrrolizine-1-carboxylic acid, 2,3-dihydro-5-benzoyl-, (+−)); and, phenylbutazone (4-butyl-1,2-diphenyl-3,5-pyrazolidinedione).

3. The method of claim 1 wherein the non-steroidal anti-inflammatory drug is selected from the group consisting of: sulindac-(2)-5-fluoro-2-methyl-1-[[p-(methyl sulfinyl) phenyl]methylene-]-1-H-indene-3-acetic acid); diflunisal (2',4'-difluoro-4-hydroxy-3-biphenylcarboxylic acid); piroxicam (4-hydroxy-2-methyl-N-2-pyridinyl-2H-1,2-benzothiazine-2-carboxamide 1,1-dioxide), an oxicam; indomethacin (1-(4-chlorobenzoyl)-5-methoxy-2-methyl-H-indole-3-acetic acid); meclofenamate sodium (N-(2,6-dichloro-m-tolyl)anthranilic acid, sodium salt, monohydrate); ketoprofen (2-(3-benzoylphenyl)-propionic acid; and tolmetin sodium (sodium 1-methyl-5-(4-methylbenzoyl-1H-pyrrole-2-acetate dihydrate).

4. The method of claim 1 wherein the non-steroidal anti-inflammatory drug is selected from the group consisting of: diclofenac sodium (2-[(2,6-dichlorophenyl)amino]benzeneatic acid, monosodium salt)); hydroxychloroquine sulphate (2-{[4-[(7-chloro-4-quinolyl)amino]pentyl]ethylamino}ethanol sulfate (1:1)); penicillamine (3-mercapto-D-valine); flurbiprofen ([1,1-biphenyl]-4-acetic acid), 2-fluoro-alphamethyl-, (+−)); cetodolac (1-8-diethyl-13,4,9, tetrahydropyrano-[3-4-13]indole-1-acetic acid; mefenamic acid (N-(2,3-xylyl)anthranilic acid; and, diphenhydramine hydrochloride (2-diphenyl methoxy-N,N-dimethylethamine hydrochloride).

5. The method of claim 1 wherein the non-steroidal anti-inflammatory drug is a COX-2 inhibitor.

6. The method of claim 1, further comprising co-administering to the patient a therapeutically effective amount of a corticosteroid.

7. The method of claim 6, wherein the corticosteroid is triamcinolone, fluocinolone, cortisone, hydrocortisone, ciclesonide, fluticasone, mometasone, betamethasone, deopomedrol, dexamethasone, budesonide, beclomethasone, predisone, methylpredinsolone, predisolone, or a combination thereof.

8. The method of claim 1, wherein the method comprises administering (+)-vinpocetine or a salt thereof to the patient by middle ear injection or by ear drops.

9. The method of claim 1, wherein (+)-vinpocetine or a salt thereof is present in a pharmaceutical composition further comprising a pharmaceutically acceptable carrier.

10. The method of claim 1, wherein (+)-vinpocetine or a salt thereof is administered in an amount of about 0.01 to about 2 mg/kg.

11. The method of claim 1, wherein (+)-vinpocetine or a salt thereof is administered in an amount of about 0.05 to about 1 mg/kg.

12. The method of claim 1, wherein (+)-vinpocetine or a salt thereof is administered in an amount of about 0.05 to about 0.5 mg/kg.

* * * * *

```
                            SEQUENCE LISTING

<160> NUMBER OF SEQ ID NOS: 30

<210> SEQ ID NO 1
<211> LENGTH: 24
<212> TYPE: DNA
<213> ORGANISM: Artificial Sequence
<220> FEATURE:
<223> OTHER INFORMATION: Synthetic 5' primer for rat TNF-alpha

<400> SEQUENCE: 1
agaacagcaa ctccagaaca ccct                                          24

<210> SEQ ID NO 2
<211> LENGTH: 24
<212> TYPE: DNA
<213> ORGANISM: Artificial Sequence
<220> FEATURE:
<223> OTHER INFORMATION: Synthetic 3' primer for rat TNF-alpha

<400> SEQUENCE: 2
tgccagttcc acatctcgga tcat                                          24

<210> SEQ ID NO 3
<211> LENGTH: 24
<212> TYPE: DNA
<213> ORGANISM: Artificial Sequence
<220> FEATURE:
<223> OTHER INFORMATION: Synthetic 5' primer for IL-1beta

<400> SEQUENCE: 3
acctgctagt gtgtgatgtt ccca                                          24

<210> SEQ ID NO 4
<211> LENGTH: 24
<212> TYPE: DNA
<213> ORGANISM: Artificial Sequence
<220> FEATURE:
<223> OTHER INFORMATION: Synthetic 3' primer for IL-1beta

<400> SEQUENCE: 4
aggtggagag ctttcagctc acat                                          24

<210> SEQ ID NO 5
<211> LENGTH: 24
<212> TYPE: DNA
<213> ORGANISM: Artificial Sequence
<220> FEATURE:
<223> OTHER INFORMATION: Synthetic 5' primer for rat CINC-1

<400> SEQUENCE: 5
agacagtggc agggattcac ttca                                          24

<210> SEQ ID NO 6
<211> LENGTH: 24
<212> TYPE: DNA
<213> ORGANISM: Artificial Sequence
<220> FEATURE:
<223> OTHER INFORMATION: Synthetic 3' primer for rat CINC-1

<400> SEQUENCE: 6
tgtggctatg acttcggttt gggt                                          24
```

```
<210> SEQ ID NO 7
<211> LENGTH: 24
<212> TYPE: DNA
<213> ORGANISM: Artificial Sequence
<220> FEATURE:
<223> OTHER INFORMATION: Synthetic 5' primer for rat MCP-1

<400> SEQUENCE: 7
tgctgtctca gccagatgca gtta                                          24

<210> SEQ ID NO 8
<211> LENGTH: 24
<212> TYPE: DNA
<213> ORGANISM: Artificial Sequence
<220> FEATURE:
<223> OTHER INFORMATION: Synthetic 3' primer for rat MCP-1

<400> SEQUENCE: 8
tacagcttct ttgggacacc tgct                                          24

<210> SEQ ID NO 9
<211> LENGTH: 24
<212> TYPE: DNA
<213> ORGANISM: Artificial Sequence
<220> FEATURE:
<223> OTHER INFORMATION: Synthetic 5' primer for rat VACM-1

<400> SEQUENCE: 9
actgtcaact gcacggtccc taat                                          24

<210> SEQ ID NO 10
<211> LENGTH: 24
<212> TYPE: DNA
<213> ORGANISM: Artificial Sequence
<220> FEATURE:
<223> OTHER INFORMATION: Synthetic 3' primer for rat VACM-1

<400> SEQUENCE: 10
acaagagctt cccggtgtc ttca                                           24

<210> SEQ ID NO 11
<211> LENGTH: 24
<212> TYPE: DNA
<213> ORGANISM: Artificial Sequence
<220> FEATURE:
<223> OTHER INFORMATION: Synthetic 5' primer for rat GAPDH

<400> SEQUENCE: 11
acaagatggt gaaggtcggt gtga                                          24

<210> SEQ ID NO 12
<211> LENGTH: 24
<212> TYPE: DNA
<213> ORGANISM: Artificial Sequence
<220> FEATURE:
<223> OTHER INFORMATION: Synthetic 3' primer for rat GAPDH

<400> SEQUENCE: 12
agcttcccat tctcagcctt gact                                          24

<210> SEQ ID NO 13
<211> LENGTH: 20
<212> TYPE: DNA
<213> ORGANISM: Artificial Sequence
<220> FEATURE:
<223> OTHER INFORMATION: Synthetic 5' primer for human TNF-alpha
```

```
<400> SEQUENCE: 13
cagagggaag agttccccag                                           20

<210> SEQ ID NO 14
<211> LENGTH: 20
<212> TYPE: DNA
<213> ORGANISM: Artificial Sequence
<220> FEATURE:
<223> OTHER INFORMATION: Synthetic 3' primer for human TNF-alpha

<400> SEQUENCE: 14
ccttggtctg gtaggagacg                                           20

<210> SEQ ID NO 15
<211> LENGTH: 25
<212> TYPE: DNA
<213> ORGANISM: Artificial Sequence
<220> FEATURE:
<223> OTHER INFORMATION: Synthetic 5' primer for human IL-1beta

<400> SEQUENCE: 15
aaacagatga agtgctcctt ccagg                                     25

<210> SEQ ID NO 16
<211> LENGTH: 24
<212> TYPE: DNA
<213> ORGANISM: Artificial Sequence
<220> FEATURE:
<223> OTHER INFORMATION: Synthetic 3' primer for human IL-1beta

<400> SEQUENCE: 16
tggagaacac cacttgttgc tcca                                      24

<210> SEQ ID NO 17
<211> LENGTH: 21
<212> TYPE: DNA
<213> ORGANISM: Artificial Sequence
<220> FEATURE:
<223> OTHER INFORMATION: Synthetic 5' primer for human IL-8

<400> SEQUENCE: 17
aacatgactt ccaagctggc c                                         21

<210> SEQ ID NO 18
<211> LENGTH: 22
<212> TYPE: DNA
<213> ORGANISM: Artificial Sequence
<220> FEATURE:
<223> OTHER INFORMATION: Synthetic 3' primer for human IL-8

<400> SEQUENCE: 18
ttatgaattc tcagccctct tc                                        22

<210> SEQ ID NO 19
<211> LENGTH: 18
<212> TYPE: DNA
<213> ORGANISM: Artificial Sequence
<220> FEATURE:
<223> OTHER INFORMATION: Synthetic 5' primer for human MCP-1

<400> SEQUENCE: 19
cccagtcacc tgctgtta                                             18

<210> SEQ ID NO 20
```

```
<211> LENGTH: 18
<212> TYPE: DNA
<213> ORGANISM: Artificial Sequence
<220> FEATURE:
<223> OTHER INFORMATION: Synthetic 3' primer for human MCP-1

<400> SEQUENCE: 20
tgctgctggt gattcttc                                                   18

<210> SEQ ID NO 21
<211> LENGTH: 24
<212> TYPE: DNA
<213> ORGANISM: Artificial Sequence
<220> FEATURE:
<223> OTHER INFORMATION: Synthetic 5' primer for human VACM-1

<400> SEQUENCE: 21
ttgctcagat tggtgactcc gtct                                            24

<210> SEQ ID NO 22
<211> LENGTH: 24
<212> TYPE: DNA
<213> ORGANISM: Artificial Sequence
<220> FEATURE:
<223> OTHER INFORMATION: Synthetic 3' primer for human VACM-1

<400> SEQUENCE: 22
ttcgtcacct tcccattcag tgga                                            24

<210> SEQ ID NO 23
<211> LENGTH: 24
<212> TYPE: DNA
<213> ORGANISM: Artificial Sequence
<220> FEATURE:
<223> OTHER INFORMATION: Synthetic 5' primer for human ICAM-1

<400> SEQUENCE: 23
ataaccgcca gcggaagatc aaga                                            24

<210> SEQ ID NO 24
<211> LENGTH: 24
<212> TYPE: DNA
<213> ORGANISM: Artificial Sequence
<220> FEATURE:
<223> OTHER INFORMATION: Synthetic 3' primer for human ICAM-1

<400> SEQUENCE: 24
cgtggcttgt gtgttcggtt tcat                                            24

<210> SEQ ID NO 25
<211> LENGTH: 24
<212> TYPE: DNA
<213> ORGANISM: Artificial Sequence
<220> FEATURE:
<223> OTHER INFORMATION: Synthetic 5' primer for mouse TNF-alpha

<400> SEQUENCE: 25
actgaacttc ggggtgatcg gtcc                                            24

<210> SEQ ID NO 26
<211> LENGTH: 22
<212> TYPE: DNA
<213> ORGANISM: Artificial Sequence
<220> FEATURE:
<223> OTHER INFORMATION: Synthetic 3' primer for mouse TNF-alpha

<400> SEQUENCE: 26
```

```
gtgggtgagg agcacgtagt cg                                              22

<210> SEQ ID NO 27
<211> LENGTH: 22
<212> TYPE: DNA
<213> ORGANISM: Artificial Sequence
<220> FEATURE:
<223> OTHER INFORMATION: Synthetic 5' primer for mouse IL-1beta

<400> SEQUENCE: 27
aacctgctgg tgtgtgacgt tc                                              22

<210> SEQ ID NO 28
<211> LENGTH: 22
<212> TYPE: DNA
<213> ORGANISM: Artificial Sequence
<220> FEATURE:
<223> OTHER INFORMATION: Synthetic 3' primer for mouse IL-1beta

<400> SEQUENCE: 28
cagcacgagg ctttttgtt gt                                               22

<210> SEQ ID NO 29
<211> LENGTH: 20
<212> TYPE: DNA
<213> ORGANISM: Artificial Sequence
<220> FEATURE:
<223> OTHER INFORMATION: Synthetic 5' primer for mouse MIP-2

<400> SEQUENCE: 29
cctgccaagg gttgacttca                                                 20

<210> SEQ ID NO 30
<211> LENGTH: 18
<212> TYPE: DNA
<213> ORGANISM: Artificial Sequence
<220> FEATURE:
<223> OTHER INFORMATION: Synthetic 3' primer for mouse MIP-2

<400> SEQUENCE: 30
ttctgtctgg gcgcagtg                                                   18
```